United States Patent [19]

Maher et al.

[11] Patent Number: 4,835,299

[45] Date of Patent: May 30, 1989

[54] PROCESS FOR PURIFYING TERTIARY ORGANOPHOSPHITES

[75] Inventors: John M. Maher; Ernst Billig, both of Charleston; David R. Bryant, South Charleston, all of W. Va.

[73] Assignee: Union Carbide Corporation, Danbury, Conn.

[21] Appl. No.: 32,906

[22] Filed: Mar. 31, 1987

[51] Int. Cl.$^4$ .......................... C07F 9/15; C07F 9/141
[52] U.S. Cl. ...................... 558/85; 558/146; 558/150
[58] Field of Search .......................... 558/150, 85, 146

[56] References Cited

U.S. PATENT DOCUMENTS

| | | | |
|---|---|---|---|
| 3,356,775 | 12/1967 | Mitchell | 260/990 |
| 3,415,906 | 12/1968 | Shepard et al. | 260/937 |
| 3,511,880 | 5/1970 | Booth | 260/604 |
| 3,527,809 | 9/1970 | Pruett et al. | 260/604 |
| 3,876,395 | 4/1975 | Cotter et al. | 260/268 PL |
| 3,917,469 | 11/1975 | Cotter et al. | 55/73 |
| 4,252,750 | 2/1981 | Buysch et al. | 260/927 R |
| 4,258,215 | 3/1981 | Dawes | 568/454 |
| 4,351,759 | 9/1982 | Spivack | 524/100 |
| 4,482,749 | 11/1984 | Dennis et al. | 568/454 |
| 4,496,768 | 1/1985 | Dennis et al. | 568/454 |
| 4,532,085 | 7/1985 | Mirviss | 260/990 |
| 4,567,306 | 1/1986 | Dennis et al. | 568/455 |
| 4,599,206 | 7/1986 | Billig et al. | 558/85 |
| 4,668,651 | 5/1987 | Billig et al. | 502/158 |
| 4,717,775 | 1/1988 | Billig et al. | 568/454 |
| 4,748,261 | 5/1988 | Billig et al. | 556/404 |
| 4,769,498 | 9/1988 | Billig et al. | 568/454 |
| 4,774,361 | 9/1988 | Maher et al. | 568/454 |

FOREIGN PATENT DOCUMENTS

694472 9/1964 Canada.
389100 7/1973 U.S.S.R..

OTHER PUBLICATIONS

"Chemical Abstracts", vol. 55, pp. 24531–24532 (1961) Imaev (Zhur. Obshchei. Khim, vol. 31, pp. 1762–1770 (1961).
"Analytical Chemistry", vol. 28, pp. 1765–1766 (1956), Bernhart et al., Determination of Di— and Trialkyl Phosphites in the Presence of Each Other.
"Chemical Abstracts", vol. 50, pp. 15342–15344 (W. Wadsworth et al., on Bicyclic Phosphites).
"J. of Organometalic Chem.", vol. 258, pp. 343–350 (1983) by P. Van leeuwen et al., on Hydroformylation of Less Reactive Olefins with Modified Rhodium Catalysts.
Translation from Izvestiya Akademii Nauk SSSR, Seriya Khimi, No. 11, pp. 2551–2552, Nov. 1967 of V. Bel'skii et al.,–"Kinetics of the Hydrolysis of Tri— and Diethyl Phosphite", (pp. 2427–2428).
Translation from Izvestiya Akademii Nauk SSSR, Seriya Khimi., No. 6, pp. 1297–1300, Jun. 1969 of V. Bel'skii et al.,–"Kinetics of the Hydrolysis of Dialkyl Phosphites".

*Primary Examiner*—Anton H. Sutto
*Attorney, Agent, or Firm*—Reynold J. Finnegan

[57] ABSTRACT

A process for purifying tertiary organophosphites by removing secondary organophosphites therefrom.

22 Claims, No Drawings

PROCESS FOR PURIFYING TERTIARY ORGANOPHOSPHITES

BRIEF SUMMARY OF THE INVENTION

1. Technical Field

This invention relates to a process for purifying tertiary organophosphites. More particularly this invention relates to a process for separating secondary organophosphites from tertiary organophosphites.

2. Background Art

Tertiary organophosphites are well known compounds and may contain three organic radicals each radical being bonded to a phosphorus atom through its own individual oxygen atom (e.g. tertiary triorganophosphites) or they may contain only two organic radicals bonded to a phosphorous atom through oxygen, one of said organic radicals being bonded through two separate oxygen atoms (i.e. each oxygen atom is bonded to a different carbon atom) and the other organic radical through its own oxygen atom (e.g. tertiary diorganophosphites). It is also possible for tertiary organophosphites to contain only one organic radical being bonded through three separate oxygen atoms (i.e. each oxygen atom being bonded to a different carbon atom of said organic radical) in which case the organic radical is obviously trivalent (e.g. tertiary monoorganophosphites). Then of course there are also tertiary organopolyphosphite compounds, i.e. compounds containing two or more of such tertiary (trivalent) phosphorus atoms wherein each phosphorus atom is connected together through a separate oxygen atom of an organic bridging radical.

Moreover tertiary organophosphites have a wide range of utility. For instance, they may be employable as stabilizers for plastics, organic polymers, resins, mineral oil, and synthetic fluids e.g. lubricating oils, and the like, as seen e.g. in U.S. Pat. No. 4,351,759. They are also one of several classes of phosphorus containing compounds described in the art as suitable for use as ligands in transition metal complex catalyzed carbonylation processes. For example they have been described as particularly useful ligands for rhodium complex catalyzed hydroformylation processes directed to producing aldehyde from an olefinic compound as seen e.g. in U.S. Pat. Nos. 3,527,809 and 4,599,206.

However tertiary organophosphites are generally manufactured by a process which also normally produces a significant amount of secondary organophosphite by-product, i.e. compounds containing a pentavalent phosphorus atom satisfied by a hydrogen radical and a double bonded oxygen radical in addition to being bonded to two individual organic radicals through two separate oxygen atoms or being bonded to only one organic radical through two separate oxygen atoms. For instance tertiary organophosphites are commonly synthesized by the reaction of phosphorus trichloride with alcohol in one or more steps and such procedures involve the formation of an organophosphoromonochloridite intermediate which is readily hydrolyzable to the secondary organophosphite by adventitious water in the process. Likewise, tertiary organophosphites, themselves, can react with water in the presence of acid to afford such secondary organophosphites.

The presence of such secondary organophosphite contamination in the desired tertiary organophosphite products may not only adversely affect the hydrolytic stability of the tertiary organophosphites, but may also adversely affect the performance of such tertiary organophosphites during their use and may even be detrimental in other ways to the particular field of use in which the tertiary organophosphite is being employed. For instance the presence of such secondary organophosphites in rhodium complex catalyzed hydroformylation using tertiary organophosphite ligands is highly undesirable. Such secondary organophosphites can react with the aldehyde product of the hydroformylation to form an aldehyde adduct of the secondary organophosphite, which in turn can readily hydrolyze to undesirable hydroxy alkyl phosphonic acid, as explained e.g. in columns 33 and 34 of U.S. Pat. No. 4,599,206. Moreover the formation of such acids during hydroformylation is an autocatalytic process. Further such secondary organophosphites and attendant reactions can adversely affect the desired stability and performance of the tertiary organophosphite ligands and may lead to catalyst deactivation and/or decomposition thus limiting the effective life of the catalyst. In addition such secondary organophosphites due to their affinity for rhodium may also cause formation of an insoluble complex with the rhodium catalyst leading to loss of valuable rhodium from the catalyst solution.

Accordingly, a simple and effective method for purifying tertiary organophosphites by separating and removing the secondary organophosphite therefrom, both before the initial use of such tertiary organophosphites and/or during the use of such tertiary organophosphites is obviously a desirable objective and would be highly beneficial to the arts.

The tendency of many secondary organophosphites to co-crystallize with tertiary organophosphites limits the efficacy of straight forward recrystallization as a means of tertiary organophosphite purification. While reducing concentrations of the secondary organophosphite to low levels can be beneficial in some circumstances, time consuming and expensive multiple straight forward recrystallizations may still leave some undesirable secondary organophosphite.

Imaev, M.G., *Zuhr. Obshchei Khim*, 31 pp. 1762-70 (1961) as reported in the two abstrances in *Chemical Abstracts*, Vol. 55, pp. 24531-32 (1961) discloses that triorganophosphites are readily hydrolyzed by pure water to secondary organophosphites and that the reaction was found to be autocatalytic with triethylphosphite. Imaev further discloses that organic and inorganic bases were found to retard the hydrolysis of trialkylphosphites, that triethylamine was a better retardant than pyridine, and postulates that the retardation was possibly due to removal of the secondary organophosphite by the formation of a salt. However no means for selectively removing the secondary organophosphite from triorganophosphite without unduly adversely hydrolyzing the triorganophosphite is seen disclosed by said abstracts.

The addition of a base compound, such as sodium hydroxide, to a trialkyl phosphite solubilized in an alcohol medium has been disclosed in the context of analytical titrations as a means of selectively hydrolyzing dialkyl phosphite impurities in the presence of trialkyl phosphite to form the salt of the corresponding primary alkyl phosphite, see Bernhart, D. N., Rattenbury, K. H., "Determination of Di and Trialkyl Phosphites in the Presence of each Other", *Analytical Chemistry*, Vol. 28, pp. 1765-1766 (1956). Although Bernhart et al discloses a method for determining the amount of dialkyl phosphite present as an impurity in trialkyl phosphite, the reference fails to disclose a means for selectively removing secondary organophosphites from tertiary organophosphites. Additionally, since this reaction is performed in an alcohol medium, transesterification of the tertiary organophosphite with the alcohol can occur.

European Patent Application Publication No. 149,894 (U.S. Pat. No. 4,567,306) is directed to a rhodium catalyzed hydroformylation process which employs a tertiary amine to stabilize a cyclic phosphite ligand having a bridgehead phosphorus atom linked to three oxygen atoms at least two of which form together with the bridgehead phosphorus atom part of a ring. Said EP No.-149,984 postulates that loss of catalyst activity during the hydroformylation is caused by degradation of the cyclic phosphite ligand due to hydrolysis by water formed as a by-product of aldolization which causes the cyclic phosphite to undergo hydrolytic reactions leading to the production of acidic materials which catalyze the ring opening of such phosphites. EP No.-149,894 discloses that the function of the tertiary amine is to react with and neutralize the acidic hydrolysis products. EP No.-149,894 further maintains that the ability of tertiary amines to stabilize the cyclic phosphites thereof is unique, in that such use was not found to preserve the stabilization of "open" phosphites such as triphenylphosphite for more than a few hours, thus indicating that the amine stabilization of triphenylphosphite as reported in a paper in *Bulletin of the Japan Petroleum Institute,* Vol. 19, No. 1, May 1977, pp. 62 to 67 by Y. Matsui [according to EP-149,894] may only help preserve the stability of a rhodium hydroformylation catalyst in the initial stage of operation. Moreover water supplied to the Examples of EP No.-149,894 in addition to the amine stabilizer appears to have been added solely to affect hydrolyzation of the desired phosphite ligand employed, in order to insure the presence of acidic hydrolysis product for exemplification of the proposed invention. In any event, neither EP No.-149,894 nor said article by Matsui are seen to teach a method whereby secondary organophosphites can be selective separated and removed from tertiary organophosphites.

The deliberate addition of water to a hydroformylation reaction medium containing a triorganophosphorus ligand such as triarylphosphite has been proposed in U.S. Pat. No. 4,258,215 to form a two-phase system. An enhancement in the reaction rate is claimed for such an aqueous treatment. Likewise the addition of water and an alkali metal or ammonium hydroxide to activate certain rhodiumphosphine complex hydroformylation catalysts as been proposed in U.S. Pat. No. 3,511,880. However neither of said patents teach how to selectively remove secondary organophosphites from tertiary organophosphites.

U.S. Pat. Nos. 3,527,809 and 4,599,206 both disclose the use of various tertiary organophosphite ligands in rhodium catalyzed hydroformylation. U.S. Pat. No. 4,599,206 further explains (in columns 33-34) the undesirability of the production of hydroxy alkyl phosphonic acid and ligand decomposition during hydroformylation and also (columns 34-49) provides a method for controlling or removing such acid via extraction with a base or preferably a basic anion exchange resin. However, neither patent teaches a method for selectively separating and removing secondary organophosphite from tertiary organophosphite ligand.

Accordingly, it is an object of this invention to provide a means for selectively separating and removing secondary organophosphites from tertiary organophosphites. Other objects and advantages of this invention will become readily apparent from the following description and appended claims.

DISCLOSURE OF INVENTION

Accordingly a generic aspect of this invention can be described as a process for separating secondary organophosphite from tertiary organophosphite which comprises (1) treating a composition consisting essentially of tertiary and secondary organophosphites dissolved in an organic solvent, with added water and a Lewis base to selectively convert the secondary organophosphite to a primary organophosphite salt and (2) separating and recovering the tertiary organophosphite from said salt.

Thus the process of this invention involves the selective conversion of the secondary organophosphite in the presence of a tertiary organophosphite in an organic solution by the treatment of added water and a Lewis base to form the corresponding primary organophosphite salt of the secondary organophosphite, followed by removal and recovery of purified tertiary organophosphite from said salt which may be easily accomplished in a variety of ways.

The process of this invention applies to the removal of secondary organophosphites from tertiary organophosphites in general from any suitable liquid composition containing said phosphites which have been organically solubilized. For instance, this invention is especially suitable for obtaining purified tertiary organophosphite by removing secondary organophosphite by-products from tertiary organophosphite production products and/or removing secondary organophosphite contaminates that may result from hydrolysis upon the storage of tertiary organophosphites. In such instances the starting compositions of this invention, which are to be treated with added water and a Lewis base, may consist essentially of only three necessary ingredients, i.e. secondary organophosphite, tertiary organophosphite and an organic solvent for said phosphites. Of course the presence of additional ingredients in the starting compositions of this invention is tolerable, provided that such additional ingredients do not have an unduly deleterious effect on the desired result of the process of this invention. For example, an additional aspect of this invention is the removal of secondary organophosphites from hydroformylation media (i.e. liquid compositions derived from hydroformylation processes containing a rhodium catalyst and a tertiary organophosphite ligand). Thus the hydroformylation media type starting compositions of the process of this invention may contain in addition to tertiary and secondary organophosphites and an organic solvent one or more additional ingredients such as may be present in the hydroformylation medium (e.g. rhodium, aldehyde, high boiling aldehyde condensation by-products, and the like). In such instances, the aldehyde and/or high boiling aldehyde condensation by-products present in the hydroformylation media may be perfectly acceptable as the organic solvent for the process of this invention, although it is to be understood that such hydroformylation media may further contain other additional organic solvents compatible with the rhodium and phosphites present therein and/or a new additional organic solvent for the phosphites of said media could be added if desired or necessary. However, as noted above, since the presence of secondary organophosphite in rhodium catalyzed hydroformylation is highly undesirable and it is obviously preferable to employ purified tertiary organophosphite right from the start of any such hydroformylation process using same, the more preferred starting compositions of this invention are not such a hydroformylation media, but rather a rhodium-free composition consisting essentially of only three necessary ingredients, i.e. secondary organophosphite, tertiary organophosphite and an organic solvent for said phosphites, as discussed above. Thus the term "rhodium-free" is employed herein to distinguish starting compositions of the process of this invention that are different from hydroformylation media starting compositions that contain rhodium.

The process of this invention may be employed to selectively remove secondary organophosphites from a variety of tertiary organophosphites. Among the tertiary organophosphites that may be purified by the process of this invention are triorganophosphites of the formula:

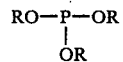  Formula I wherein each R is independently a substituted or unsubstituted monovalent hydrocarbon radical, such as trialkyl phosphites, dialkylaryl phosphites, alkyldiaryl phosphites, triarylphosphites and the like. For example, trimethyl phosphite, triethyl phosphite, butyldiethyl phosphite, tri-n-propyl phosphite, tri-n-butyl phosphite, tri-2-ethylhexyl phosphite, tri-n-octylphosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, and the like. The most preferred triorganophosphite is triphenylphosphite. Illustrative corresponding secondary organophosphites of such triorganophosphites are those of the formula $(RO)_2P(O)H$ wherein each R is the same as defined above.

Other suitable tertiary organophosphites that can be purified by the process of this invention are diorganophosphites of the formula

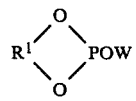  Formula II wherein, $R^1$ represents a divalent organic radical and W represents a substituted or unsubstituted monovalent hydrocarbon radical. Illustrative corresponding secondary diorganophosphites of such tertiary diorganophosphites are those of the formula

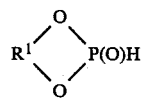  Formula III wherein $R^1$ is the same as defined above.

Representative divalent radicals represented by $R^1$ in Formula II above include those wherein $R^1$ may be a divalent acyclic radical or a divalent aromatic radical. Illustrative divalent acyclic radicals are e.g. alkylene, alkylene-oxy-alkylene, alkylene-NX-alkylene wherein X is hydrogen or a monovalent hydrocarbon radical, alkylene-S-alkylene, and cycloalkylene radicals; and the like. The more preferred acyclic radicals are divalent alkylene radicals such as disclosed more fully e.g. in U.S. Pat. Nos. 3,415,906 and 4,567,306, and the like, the entire disclosures of which are incorporated herein by reference thereto. Illustrative divalent aromatic radicals are e.g. arylene, bi-arylene, arylene-alkylene, arylene-alkylene-arylene, arylene-oxy-arylene, arylene-oxy-alkylene, arylene-NX-arylene and arylene-NX-alkylene wherein X is hydrogen or a monovalent hydrocarbon radical, arylene-S-alkylene, and arylene-S-arylene radicals; and the like. More preferably $R^1$ is a divalent aromatic radical.

Representative of a more preferred class of tertiary diorganophosphites are diorganophosphites of the formula

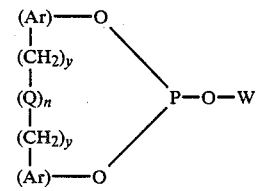  Formula IV wherein W is a substituted or unsubstituted monovalent hydrocarbon radical, Ar is a substituted or unsubstituted aryl radical, each Ar being the same or different, each y individually has a value or 0 or 1, Q is a divalent bridging group selected from the group consisting of $\geq CR^3R^4-$, $-O-$, $-S-$, $-NR^5-$, $SiR^6R^7-$ and $-CO-$, wherein each $R^3$ and $R^4$ is independently selected from the group consisting of hydrogen, alkyl radicals having 1 to 12 carbon atoms, phenyl, tolyl and anisyl, wherein each $R^5$, $R^6$ and $R^7$ are independently hydrogen or a methyl radical, and n has a value of 0 or 1. Formula IV type diorganophosphites are described in greater detail, e.g., in U.S. Pat. No. 4,599,206 and U.S. application Ser. No. 865,061 filed May 20, 1986, now U.S. Pat. Nos. 4,668,651, and 4,769,498, the entire disclosures of which are incorporated herein by reference thereto.

Among the even more preferred diorganophosphites are those of the formula

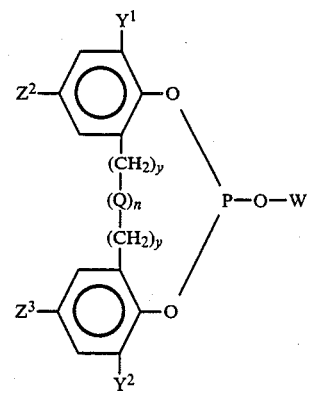  FORMULA V wherein Q is $-CR^1R^2$ and each $R^1$ and $R^2$ radical individually represents a radical selected from the group consisting of hydrogen and alkyl; wherein each y individually has a value of 0 or 1, and n has a value of 0 to 1; wherein W represents in unsubstituted or substituted monovalent hydrocarbon radical selected from the group consisting of alkyl radicals having from 1 to 18 carbon atoms, (such as primary, secondary and tertiary alkyl radicals e.g. methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, decyl, octadecyl, and the like) as well as, aryl radicals, such as alpha-naphthyl, beta-naphthyl, and aryl radicals of the formula

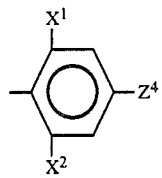

and wherein each $X^1$, $X^2$, $Y^1$, $Y^2$, $Z^2$, $Z^3$, and $Z^4$ group individually represents a radical selected from the group consisting of hydrogen, an alkyl radical having from 1 to 8 carbon atoms, substituted or unsubstituted aryl, alkaryl, aralkyl and alicyclic radicals (e.g. phenyl, benzyl, cyclohexyl, 1-methylcyclohexyl, and the like), hydroxy (—OH), and an ether (i.e oxy) radical such as —$OR^8$ wherein $R^8$ is an alkyl radical of 1 to 18 carbon atoms.

Illustrative diorganophosphites include e.g. (t-Bu is a tertiary butyl radical; $C_9H_{19}$ is a nonyl radical and Ph is a phenyl radical)

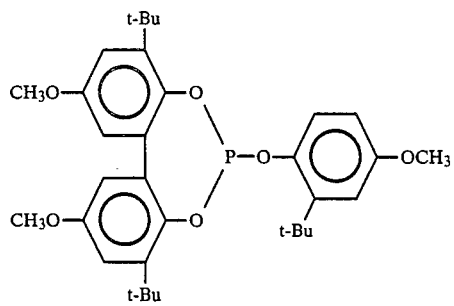

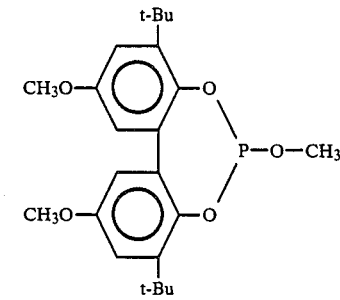

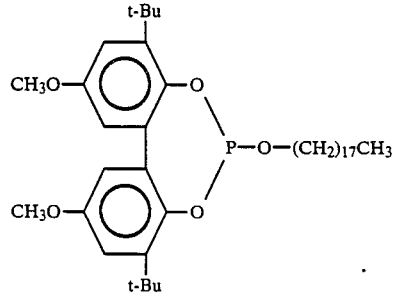

-continued

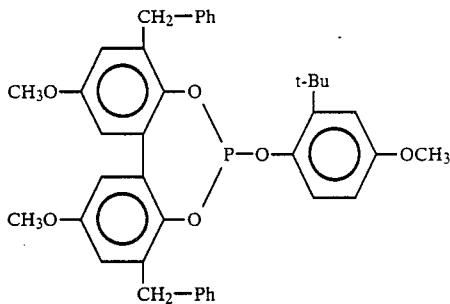

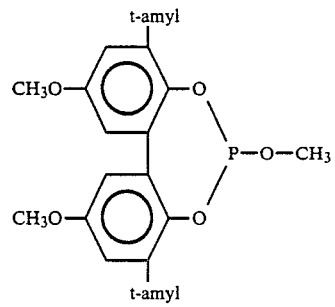

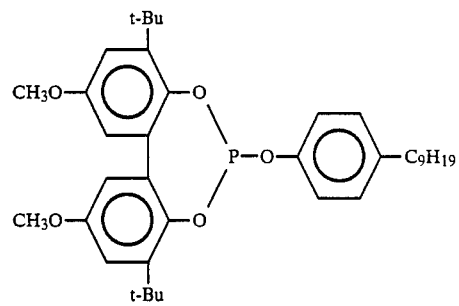

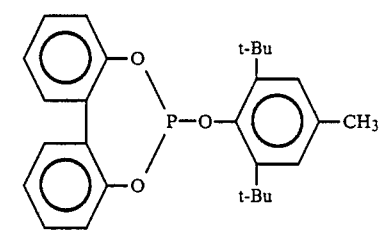

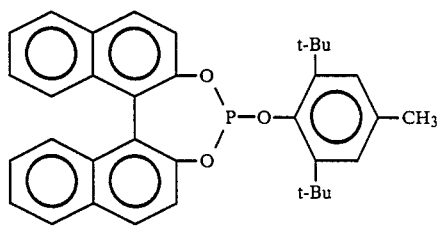

-continued

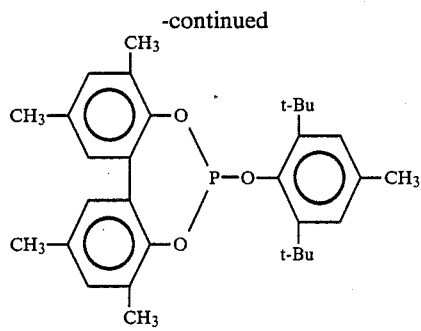

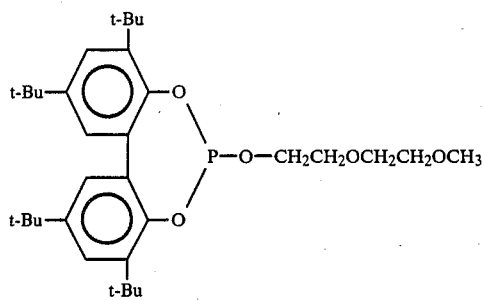

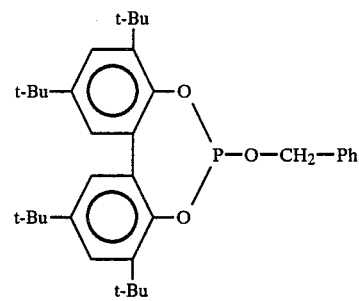

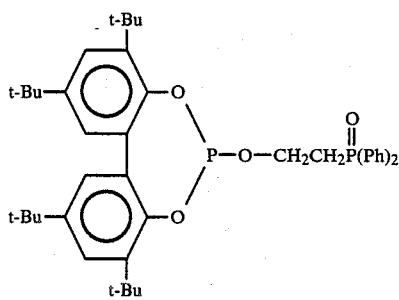

Still another group of tertiary organophosphites that may be purified by the process of this invention are tertiary organopolyphosphites. Such phosphites contain two or more of such tertiary (trivalent) phosphorus atoms such as those of the formula

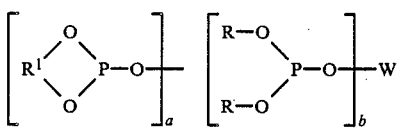

Formula VI wherein W represents a substituted or unsubstituted m-valent hydrocarbon radical, wherein $R^1$ is the same as defined in Formula II above, wherein each R is the same as defined in Formula I above, wherein a and b can each have a value of 0 to 6 with the proviso that the sum of a+b is 2 to 6 and m equals a+b. Illustrative tertiary organopolyphosphites include bisphosphites such as those of the formulas

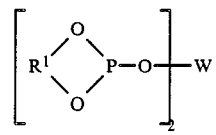

Formula VII wherein $R^1$ is a divalent organic radical as defined in Formula II above and wherein W is a substituted or unsubstituted divalent hydrocarbon radical; and

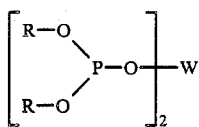

Formula VIII wherein each R is independently a substituted or unsubstituted monovalent hydrocarbon radical, and wherein W is a substituted or unsubstituted divalent hydrocarbon radical; and

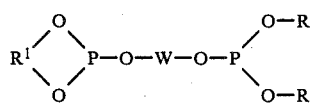

Formula IX wherein $R^1$ is a divalent organic radical as defined in Formula II above, wherein each R is independently a substituted or unsubstituted monovalent hydrocarbon radical, and wherein W is a substituted or unsubstituted divalent hydrocarbon radical. Thus for example depending on the particular tertiary organophosphite involved illustrative corresponding secondary organobisphosphites are those having the formulas $(RO)_2P(O)H$ and

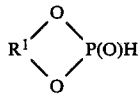

Formula X wherein R and $R^1$ are the same as defined above.

Representative of a preferred class of tertiary organophosphites suitable for use herein are bisphosphites of the formula

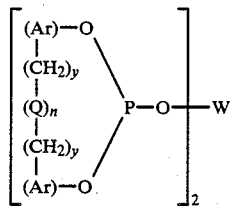

Formula XI wherein each Ar group represents an identical or different, substituted or unsubstituted aryl radical; wherein W represents a divalent radical selected from the group consisting of alkylene, alkylene-oxy-alkylene, arylene and arylene—$(CH_2)Y \geq (Q)n \geq (CH_2)Y \geq$ arylene, wherein each arylene radical is the same as Ar defined above; wherein each Q individually represents a divalent bridging group selected from the class consisting of $\geq CR^3R^4-$, $-O-$, $-S-$, $-NR^5-$, $-SiR^6R^7$ and $-CO-$, wherein each $R^3$ and $R^4$ radical individually represents a radical selected from the group consisting of hydrogen and alkyl, wherein each $R^5$, $R^6$, and $R^7$ radical individually represents $-H$ or $-CH_3$; wherein each y and n individually has a value of 0 or 1. Formula XI type bisphosphites are described in greater detail e.g., in U.S. Pat. No. 4,351,759 and U.S. patent applications, Ser. Nos. 772,859 and 12329 filed Sept. 5, 1985 and Feb. 9, 1987, the entire disclosures of which are incorporated herein by reference thereto.

Among the even more preferred bisphosphites of Formula XI above are those of the formula Formula XII

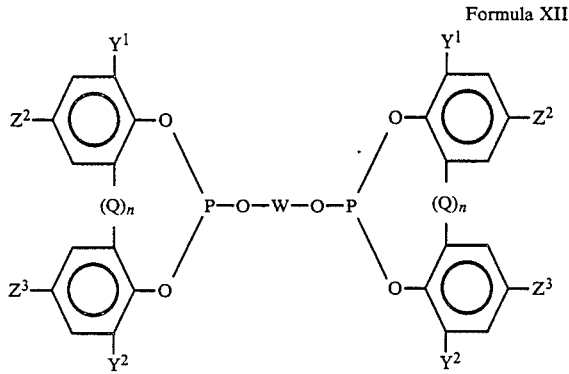

wherein Q is $-CR^1R^2$ wherein each $R^1$ and $R^2$ radical individually represents a radical selected from the group consisting of hydrogen and alkyl; wherein n has a value of 0 or; wherein each $Y^1$, $Y^2$, and $Z^2$, and $Z^3$ group individually represents an identical or different radical selected from the group consisting of hydrogen, an alkyl radical having from 1 to 18 carbon atoms, substituted or unsubstituted aryl, alkaryl, aralkyl and alicyclic radicals, hydroxy ($-OH$) and an alkoxy radical e.g. $-OR^8$ wherein $R^8$ is an alkyl radical of 1 to 18 carbon atoms; and wherein W is a divalent radical selected from the group consisting of alkylene, and substituted or unsubstituted phenylene, naphthylene, naphthylene- $-(Q)-_n$naphthylene and phenylene $-(Q)_n-$phenylene radicals wherein Q and n are the same as defined above. Preferably W is a divalent radical selected from the group consisting of 1,2-ethylene, substituted phenylene, substituted phenylene—(Q-$)_n$—phenylene radicals, 1,4-naphthylene and 1,5-naphthylene. Moreover, the preferred substituents on such phenylene and/or phenylene—$(Q)_n$—phenylene radicals are preferably radicals selected from the group consisting of alkyl and alkoxy radicals.

Illustrative bisphosphites of Formula XI above include, e.g.

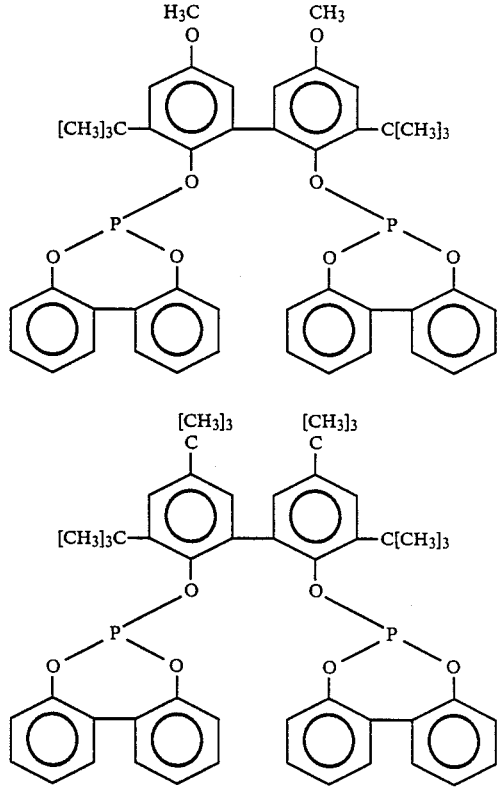

-continued
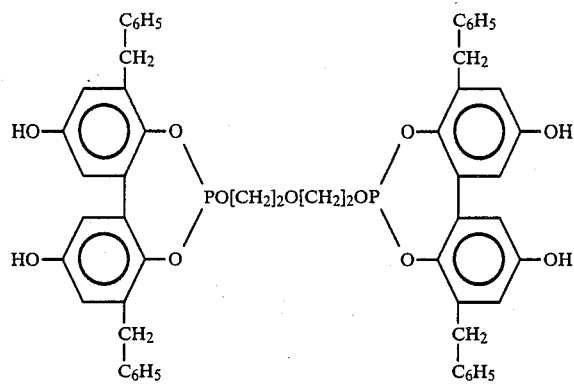
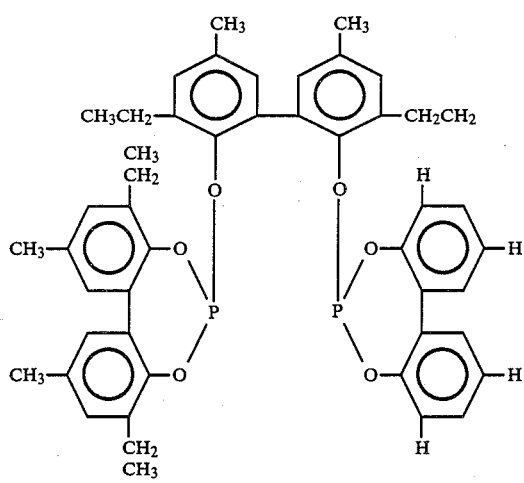
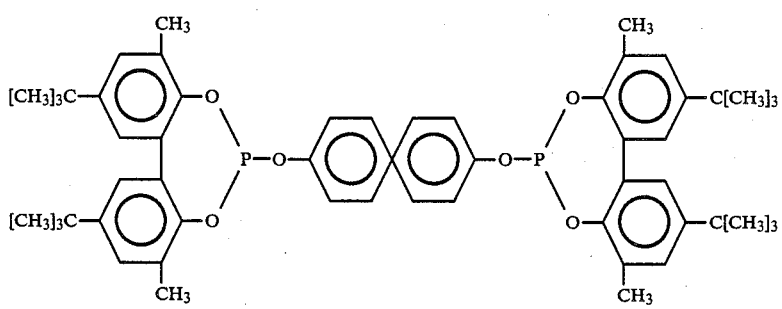
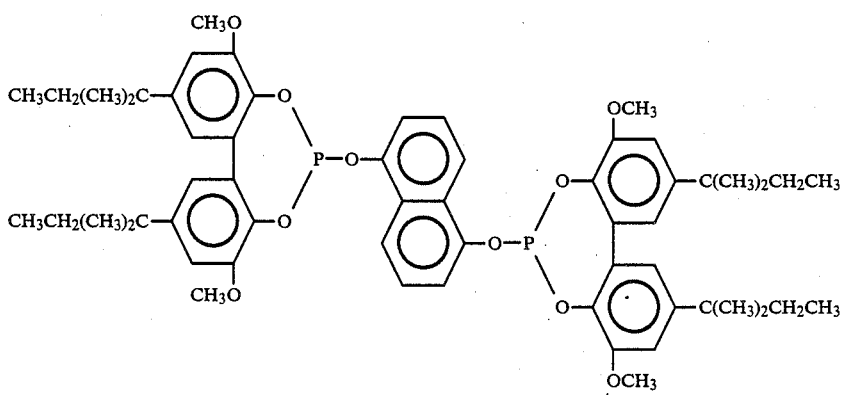

-continued
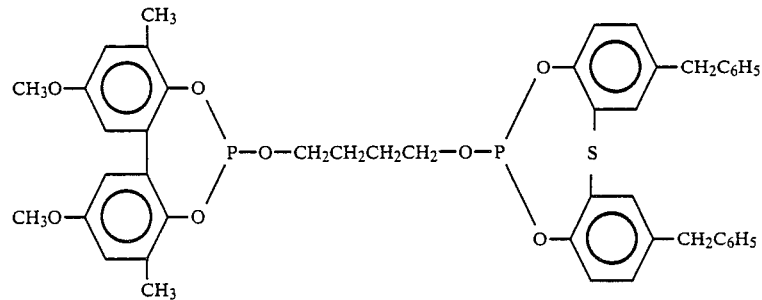
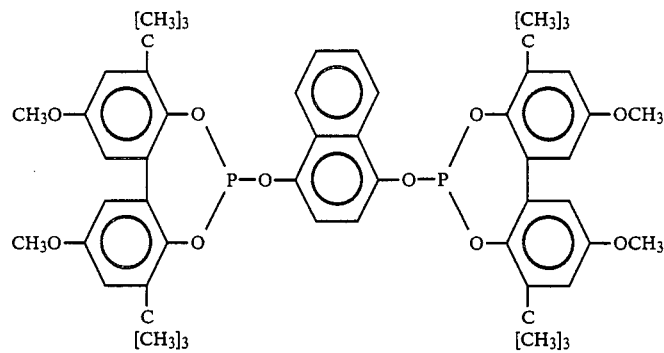
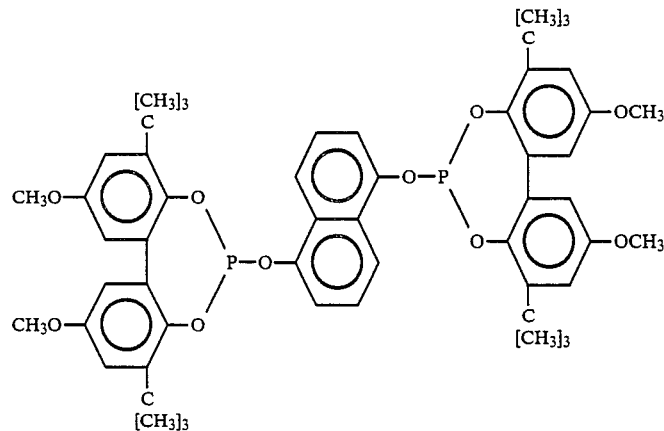
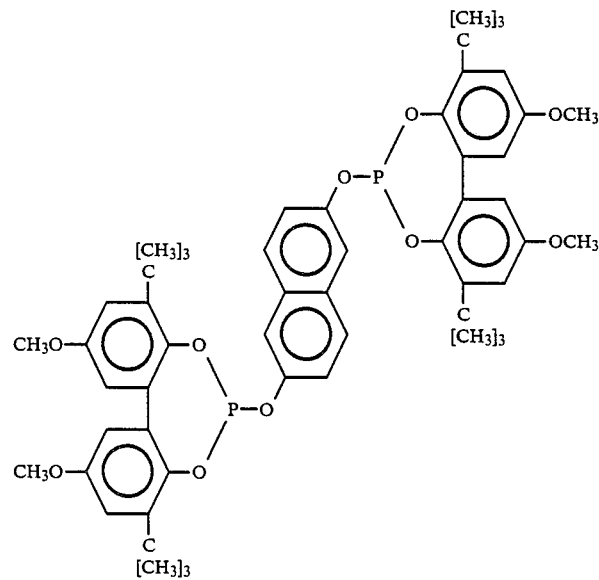

Representative of yet another preferred class of tertiary organobisphosphites are bisphosphites of the formula

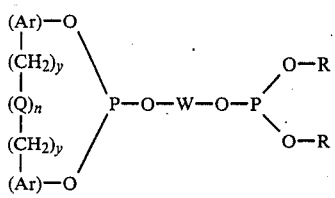

Formula XIII wherein each Ar group represents an identical or different, substituted or unsubstituted aryl radical; wherein W represents a divalent radical selected from the group consisting of alkylene, arylene and -arylene —(CH$_2$)Y—(Q)n—(CH$_2$)Y—arylene-, wherein each arylene radical is the same as Ar defined above; wherein each Q individually represents a divalent bridging group selected from the class consisting of —CR$^3$R$^4$—, —O—, —S—, —NR$^5$—, —SiR$^6$R$^7$— and —CO—, wherein each R$^3$ and R$^4$ radical individually represents a radical selected from the group consisting of hydrogen, and alkyl, wherein each R$^5$, R$^6$, and R$^7$ radical individually represents —H or —CH$_3$; wherein each y and n individually has a value of 0 or 1; and wherein each R group individually represents a radical selected from the group consisting of substituted or unsubstituted monovalent hydrocarbon radicals such as alkyl, aryl, alkaryl, aralkyl and alicyclic radicals. Formula XIII type bisphosphites are described in greater detail e.g., in U.S. patent application, Ser. No. 772,891 filed Sept. 5, 1985, now U.S. Pat. No. 4,769,498, the entire disclosure of which is incorporated herein by reference thereto.

Among the even more preferred bisphosphites of Formula XIII above are those of the formula

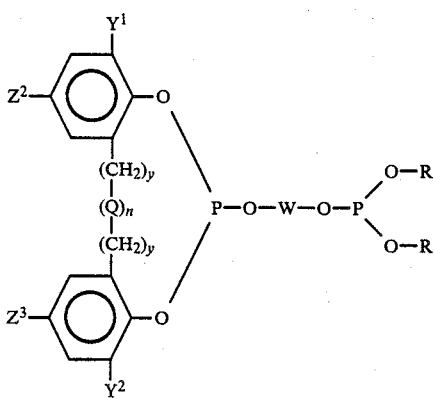

Formula XIV wherein each R group individually represents an identical or different, unsubstituted or substituted monovalent hydrocarbon radical selected from the group consisting of alkyl radicals having from 1 to 18 carbon atoms, (such as primary, secondary and tertiary alkyl radicals e.g. methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, decyl, octadecyl, and the like) as well as, aryl radicals, such as alpha-naphthyl, beta-naphthyl, and aryl radicals of the formula

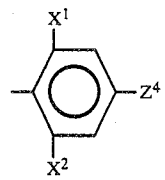

wherein Q is —CR$^1$R$^2$ wherein each R$^1$ and R$^2$ radical individually represents a radical selected from the group consisting of hydrogen and alkyl; wherein n has a value of 0 or 1; wherein each Y$^1$, Y$^2$, X$^1$, X$^2$, Z$^2$, Z$^3$ and Z$^4$ group individually represents an identical or different radical selected from the group consisting of hydrogen, an alkyl radical having from 1 to 18 carbon atoms, substituted or unsubstituted aryl, alkaryl, aralkyl and alicyclic radicals, hydroxy (—OH), and an alkoxy radical e.g. —OR$^8$ wherein R$^8$ is an alkyl radical of 1 to 18 carbon atoms; and wherein W is a divalent radical selected from the group consisting of alkylene, and substituted or unsubstituted phenylene, naphthylene, naphthylene—(Q)$_n$—naphthylene and phenylene —(Q)$_n$—phenylene radicals wherein Q and n are the same as defined above. Preferably W is a divalent radical selected from the group consisting of 1,2-ethylene, substituted phenylene, substituted phenylene—(Q)$_n$—phenylene radicals, 1,4-naphthylene and 1.5-naphthylene. Moreover, the preferred substituents on such phenylene and/or phenylene—(Q)$_n$—phenylene radicals are preferably radicals selected from the group consisting of alkyl and alkoxy radicals.

Illustrative bisphosphites of Formula XIII above include, e.g.

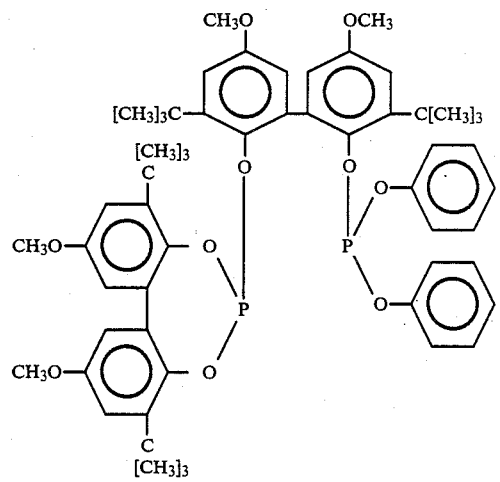

-continued
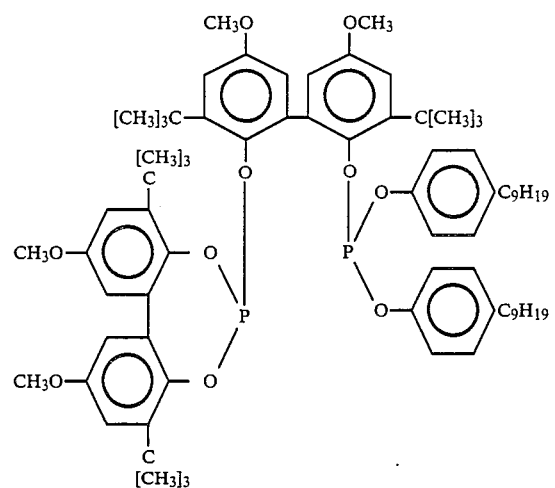
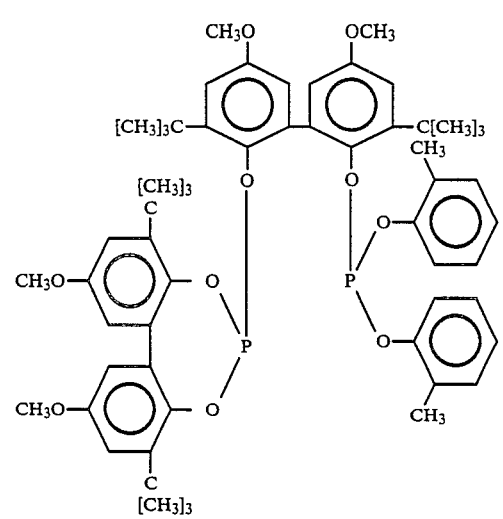
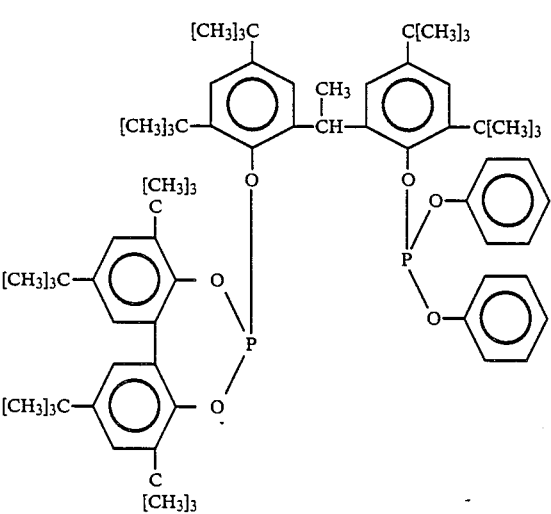
-continued
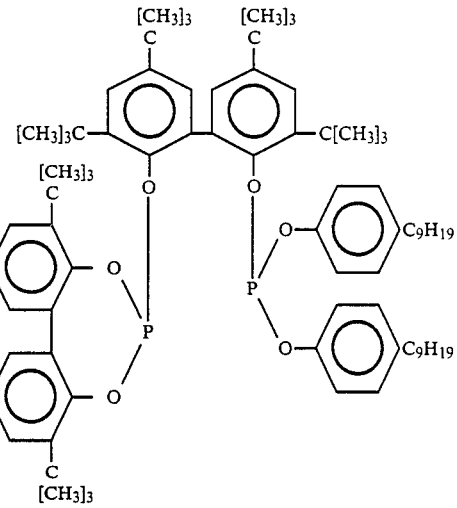
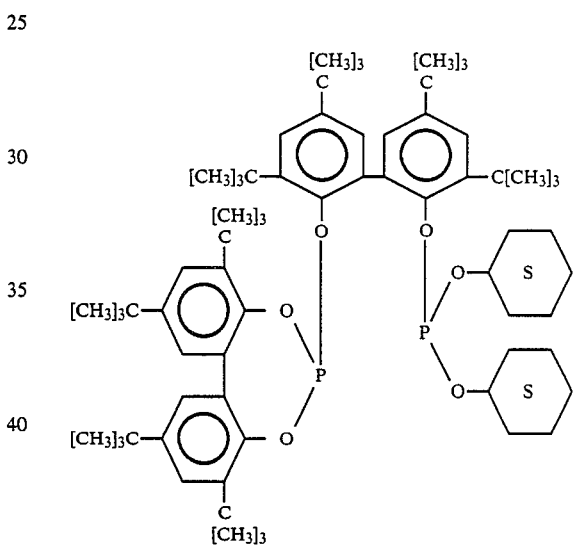
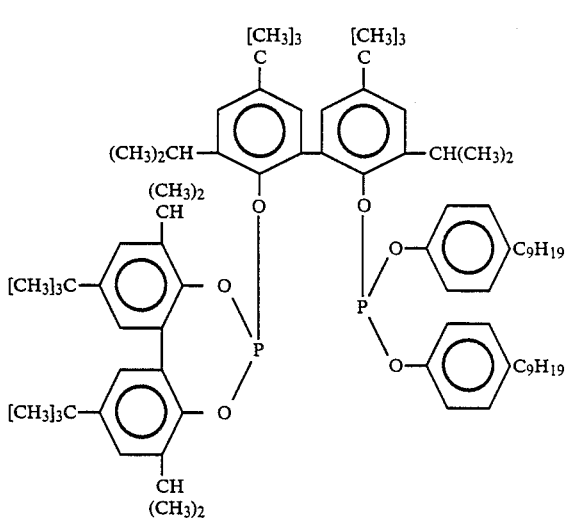

-continued

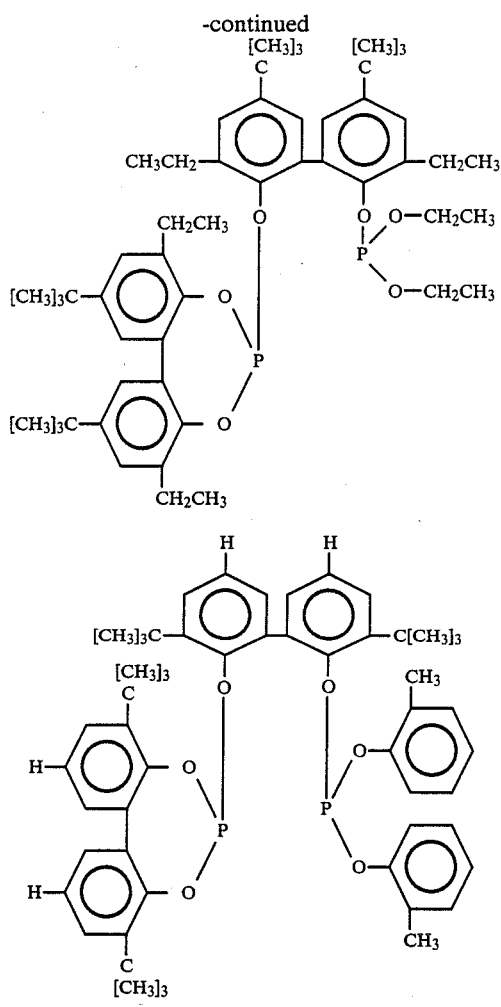

Representative of still another preferred class of tertiary organobisphosphites are bisphosphites of the formula

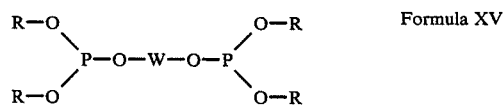

Formula XV wherein W and each R group individually represents a radical as defined in the Formula XIII above.

Finally another group of tertiary organophosphites that may be purified by the process of this invention are tertiary mono-organophosphites of the formula

Formula XVI wherein $Z^5$ represents a trivalent organic radical.

Representative trivalent radicals represented by $Z^5$ in Formula XVI above include trivalent acyclic radicals and trivalent cyclic radicals, such as trivalent alkylene or trivalent cycloalkylene radicals. Illustrative trivalent alkylene radicals may include e.g. the trivalent alkylene derived from 1,2,2-trimethylolpropane; and the like; while illustrative cycloalkylene radicals may include the trivalent cyclohexylene radical derived from 1,3,5-trihydroxy cyclohexane; and the like. Illustrative corresponding secondary organophosphites of such mono-organophosphites are those of the formula

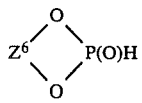

Formula XVII wherein $Z^6$ corresponds to a divalent organic radical derived from $Z^5$ in Formula XVI. Formula XVI mono-organophosphites are described in greater detail e.g. in U.S. Pat. No. 4,567,306, the entire disclosure of which is incorporated herein by reference thereto.

Any organic solvent capable of providing a solvent medium at the process temperatures employed in which both the particular tertiary organophosphite and secondary organophosphite involved are solubilized may be suitable for use in the practice of this invention. Included among the solvents suitable for use in this invention are compounds such as acetonitrile, tetrahydrofuran, toluene, benzene, xylene, ethers, esters, cycloaliphatics, aldehydes, higher boiling aldehyde condensation by-products, and the like. Of course, it is obvious that since the object of this invention is to obtain as much purified tertiary organophosphite as possible, organic solvents which may unduly transesterify the particular tertiary organophosphite employed such as simple primary alcohols and organic acids are generally deemed to be undesirable, although they may possibly be used, if desired. Likewise the use of water, should be avoided. In general the preferred solvents are acetonitrile and tetrahydrofuran, and when treating a hydroformylation media, e.g. a rhodium catalyst recycle solution, aldehyde and/or higher boiling aldehyde condensation by-products are the preferred solvents. The amount of solvent employed is not narrowly critical and need only be that minimum amount sufficient to solubilize the phosphites involved and provide a suitable solvent medium for the starting phosphite containing composition to be treated by this invention. Of course, amounts in excess of such minimum solubilizing amounts are generally preferred, the upper amount of solvent employed of course merely being dependent upon the amount and particular solubility of the phosphites employed, compositional make-up of the starting composition, economic constraints, and the like. In general the amount of solvent employed may range from about 5 to about 99 percent by weight or higher based on the total weight of the starting composition to be treated by this invention.

In addition to water another added critical ingredient of this invention is the Lewis base. Lewis bases are well known in the art and in keeping with their common definition, as used herein, the term "Lewis Base" means a compound possessing an unshared pair of electrons. Any suitable Lewis base may be employed such as, e.g., alkali metal, alkaline earth metal, ammonium, quaternary ammonium and quaternary phosphonium, hydroxides, carbonates, bicarbonates, carboxylates, and the like; amines, such as e.g., primary, secondary, tertiary, and heterocyclic amines, as well as resinous compositions having such Lewis base functionality incorporated into their polymeric structure. Illustrative bases include e.g., sodium hydroxide, potassium hydroxide, barium carbonate, barium hydroxide, calcium hydroxide, ammonium hydroxide, sodium benzoate, sodium carbonate, sodium bicarbonate, sodium carboxylate, ethylamine, diethylamine, triethylamine, tripropylamine, triethanolamine, dibutylamine, tributylamine, trihexylamine, trioctylamine, dimethylpropylamine, dimethylhexadecylamine, methyldioctylamine, dimethyl-sec-butylamine, imidazole, piperazine, N,N-dimethylaniline, N,N-diethylaniline, N,N-dimethyl-1-naphthylamine, N,N,N',N'-tetramethylethylene diamine, triethylene diamine (i.e., 1,4-diazabicyclo-[2,2,2]-octane), tetraethylammonium benzoate, tetraethylphosphonium acetate, and the like, as well as resinous compositions having Lewis base functionality incorporated into their polymeric structure such as e.g. solid amine-resins, i.e., solid polymers, including homopolymers, that have pendant amino groups attached to and/or incorporated in their polymeric backbone, and which may be of gel, particulate or macroreticular type. Such types of solid amine-resins and/or methods for their manufacture are well known in the art as seen e.g. by U.S. Pat. Nos. 3,876,395 and 3,917,469 the disclosures of which are incorporated herein by reference thereto. Illustrative of the more preferred Lewis bases are tertiary amines, especially triethylamine and solid amine-resins such as amine-Amberlyst® resins, e.g. Amberlyst® A-21 and A-27, (commercially available from Rohm and Haas Corporation) and amine-Puramer® resins, e.g. Puramer® S, (commercially available from Union Carbide Corporation), and the like. Moreover the Lewis bases employable herein may be soluble or insoluble in the solvent of the starting composition. For instance as a general rule tertiary amine bases such as triethylamine are soluble in the solvents employable herein, while solid-amine resins such as discussed above are insoluble.

Of course it is to be understood that the particular Lewis base employed in a given process of this invention must be able to effect the conversion of the secondary organophosphite to its corresponding primary organophosphite salt under the reaction conditions employed without unduly adversely affecting the tertiary phosphite and that not all Lewis bases may be suitable in every given instance. Thus the choice of the Lewis base to be employed may be dependent in part upon the particular tertiary organophosphite and/or secondary organophosphite present in the starting composition to be treated. For instance if the salt of the primary organophosphite produced by the process of this invention is itself capable of catalyzing the decomposition of the tertiary organophosphite, then the use of an insoluble Lewis base is recommended, e.g. as in the case of purifying triphenylphosphite. Moreover, in contrast to soluble Lewis bases, insoluble Lewis bases have been found to be generally employable in the process of this invention irrespective of the tertiary and secondary organophosphites present in the starting composition.

Likewise the bascity of the Lewis bases required to effect the formation of the primary organophosphite salt during the process of this invention may also be subject to variation depending in part on the particular secondary organophosphite present in the starting composition. For example, secondary organophosphites of trialkylphosphites typically require the use of stronger Lewis bases to produce a primary organophosphite than do secondary organophosphites of triarylphosphites and thus may require a strong Lewis base such as sodium hydroxide or an insoluble Lewis base e.g. a solid amine-resin to be effective. Similarly the strength of the Lewis bases required in a given process of this invention wherein the particular secondary organophosphite is derived from a diorganophosphite, an organopolyphosphite and/or a mono-organophosphite such as depicted e.g. by Formulas II, V and XI above may be dependent upon the structural make-up of the particular phosphite involved. As a general rule it is recommended that when anionic (negatively charged) Lewis bases are employed their pKa value be at least about 4 and when neutral (uncharged) Lewis bases are employed their pKa value be at least about 6 and more preferably at least about 7.

Moreover, the choice of the Lewis base to be employed is also dependent in part upon the nature of the starting composition and the method in which one desires to separate and recover the desired purified tertiary organophosphite from the primary organophosphite salt of the Lewis base that is formed during the water and Lewis base treatment of the starting composition. For instance the process of this selective conversion of the secondary organophosphite via hydrolysis (reaction with the water) to the corresponding primary organophosphite which reacts with the Lewis base to form the primary organophosphite salt, said salt being soluble or insoluble in the reaction solution depending upon whether a soluble or insoluble Lewis base was used. Of course it is also to be understood that this invention also requires the separation and recovery of the tertiary organophosphite from the primary organophosphite salt in order to obtain the desired purified tertiary organophosphite. Thus for instance, in rhodium-free type starting compositions such as those containing essentially only the solubilized tertiary and secondary organophosphites, soluble Lewis bases are preferred when it is desired to obtain the purified tertiary organophosphite in solid or crystalline form. For example, it has been found that the tertiary organophosphite may be readily recrystallized and recovered from the treated reaction solution, leaving the solubilized primary organophosphite salt behind in solution. Of course, insoluble Lewis bases may also be employed in the treatment of such starting compositions, however in such instances since the primary organophosphite salt is also insoluble, the purified tertiary organophosphite is obtained as a liquid e.g. by filtration or any other suitable method. Further, when the starting composition contains rhodium such as in the case of a hydroformylation medium, e.g., a rhodium catalyst recycle solution, it is preferred to employ an insoluble Lewis base so that both purified tertiary organophosphite as well as the most valuable soluble rhodium catalyst and/or rhodium values can be obtained in solution form and reused as desired. While possible, it is obviously not economically desirable to use a soluble Lewis base for such rhodium containing starting compositions, since recrystallization of the purified tertiary organophosphite would leave the soluble rhodium catalyst and/or rhodium values behind in solution along with the undesirable soluble primary organophosphite salt. As a general rule the preferred Lewis bases employable herein are soluble tertiary amines, especially triethylamine, and insoluble solid amine-resins such as discussed above.

Finally, the success of this invention is predicated on adding water as well as a Lewis base to the phosphite containing starting composition that is to be treated. By this invention the selective conversion of secondary organophosphites is carried out by the controlled addition of both water and a Lewis base to the tertiary organophosphite containing solvent medium. Such is a surprising discovery since the use of either only added Lewis base or only added water, without the other, does not achieve the desired results of this invention. In general, it is preferred to add at least one mole equivalent of Lewis Base and at least one mole equivalent of water, per mole equivalent of secondary organophosphite contained in the starting composition to be treated. However, lesser amounts of water and Lewis base may be added if less than total conversion of the secondary organophosphite is desired. However, for purposes of this invention, when less than one mole of Lewis base is added per mole of secondary organophosphite present in the starting composition, it is recommended that the amount of water added thereto should not exceed the amount of Lewis base added, since when such low amounts of Lewis base are employed, the addition of water in an amount in excess of the molar equivalent of Lewis base can result in the rapid decomposition of the desired tertiary organophosphite. On the other hand, it has been surprisingly discovered that when the mole amount of Lewis base employed is at least equivalent to, or more preferably greater than, the mole amount of secondary organophosphite present in the starting compositions, amounts of water in excess of the amount of Lewis base employed are not unduly detrimental to the tertiary organophosphite, but indeed are even generally preferred. While bearing in mind that the generally desired purpose of this invention is to insure complete conversion of secondary organophosphite to primary organophosphite salt the mole ratio of added Lewis Base to secondary organophosphite present in the starting composition may be as little as at least 0.5 to 1, while preferably said mole ratio is at least 1:1 and more preferably at least 1.5:1. Likewise, the mole ratio of added water to secondary organophosphite present in the starting composition may also be as little as at least 0.5 to 1, while preferably said mole ratio is at least 1:1 and more preferably at least 1.5:1, with the added recommendations that when (a) the mole ratio of Lewis Base to secondary organophosphite is less than 1:1, the amount of water added should preferably not exceed the amount of Lewis base employed; and when (b) the mole ratio of Lewis base to secondary organophosphite is 1:1 or greater, the amount of water added be at least the same, and more preferably in excess to the amount of Lewis base employed. Of course it is to be understood that when an excess amount of Lewis base is employed the amount of water added need not necessarily be greater than the amount of Lewis Base employed for it could also be lower than the amount of Lewis base employed if desired. The upper amounts of added Lewis base and added water are otherwise not critical to the process of this invention and in general any excess amount of Lewis base and added water may be employed as desired, such amounts for the most part being merely dependent upon economic constraints and the desirability to maintain the phosphites involved in solution. In general, amounts of Lewis base ranging from 0.5 up to 50 moles per mole of the secondary organophosphite contained in the starting composition along with amounts of added water ranging from 0.5 up to 500 moles per mole of secondary phosphite contained in the starting composition should be sufficient for most purposes. Of course, it should also be clear that when the starting composition contains solubilized rhodium and it is desired to recycle the solution containing said rhodium and purified tertiary organophosphite back to the hydroformylation reactor; the amount of added water employed should preferably be as low as possible and still be as effective as desired, since water is not normally desirable, but detrimental to hydroformylation process and thus will preferably have to be removed from the aqueous solution containing the purified tertiary organophosphite and rhodium before said solution can be reintroduced into the hydroformylation reactor.

In any event, it should be clear, that the optimum Lewis base and optimum amounts of same along with the optimum amounts of added water employable in a given situation may be readily determined by routine experimentation using the guidelines provided by this invention.

In general, the treatment of the phosphite containing starting compositions of this invention may be carried out a reaction temperature of from about room temperature (e.g. 25° C.) up to the reflux temperature of the reaction mixture. Moreover, the addition of the Lewis base and water to the starting composition, as well as the reaction treatment process, are preferably conducted under an inert, e.g. nitrogenous, atomsphere to avoid possible loss of tertiary organophosphite through oxidation. Likewise, when forming the reaction mixture, the co-addition of Lewis base and water, or more preferably the sequential addition of the Lewis base followed by the added water is recommended in order to avoid possible hydrolysis of the tertiary organophosphite. While the water can be added to the starting composition prior to the Lewis base, if desired, when done in this order, it is recommended to add the Lewis base as soon as possible after the addition of such water.

As noted above, the subject invention encompasses the removal of secondary organophosphite from rhodium containing compositions derived from a hydroformylation process that employs rhodium complex catalysts and tertiary organophosphite as the ligand. Accordingly, it is to be understood that the subject invention provides a means for ridding such rhodium complex catalyst containing solutions, that may also contain solubilizing amounts of aldehyde and/or higher boiling aldehyde condensation by-products, of such undesirable secondary organophosphites. Moreover, it is believed that the subject invention can be employed to also remove aldehyde adducts of the secondary organophosphites at the same time by the same mechanism that such secondary organophosphites are removed. Thus, another generic aspect of this invention comprises passing all or part of the liquid effluent stream of a continuous rhodium catalyzed hydroformylation process, e.g. the liquid recycle stream of such a process, through any suitable solid bed of amine-resin (Lewis base) to remove some or all of such secondary organophosphites and the aldehyde adducts thereof prior to reincorporation of the purified liquid into the hydroformylation reactor. The requirement of adding water to the composition liquid to be treated would of course be satisfied by incorporation of the water in the amine-resin bed or by the addition of water just prior to passing the contaminated phosphite containing liquid solution through said amine-resin bed. Of course, if desired, more than one such amine-resin bed may be employed and any such bed may be easily removed and/or replaced as desired. Moreover, excess water in the purified rhodium-tertiary phosphite containing liquid may be removed by any suitable means and such is recommended prior to reincorporation of the purified liquid to the hydroformylation reactor. Further, the amount of added water and amine-resin bed employed may be adjusted, as desired, to compensate for the amount of aldehyde adducts of secondary organophosphites that may also be present in the starting composition and which are also desired to be removed by the process of this invention.

The following examples are illustrative of the present invention and are not to be regarded as limitative. Moreover as reported in the examples the following designations and conditions are used.

Phosphite A - A tertiary organophosphite of the formula:

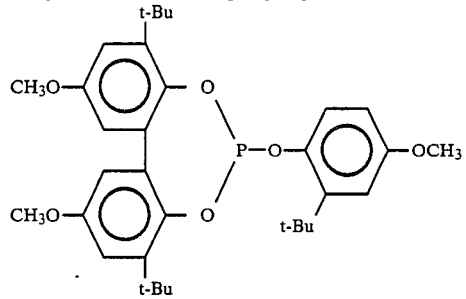

Phosphite B - A tertiary organophosphite of the formula:

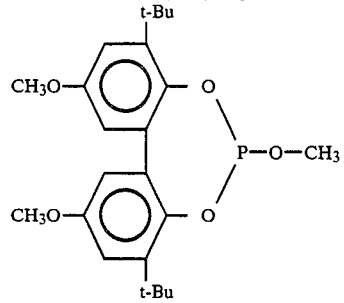

Phosphite C - A tertiary organophosphite of the formula:

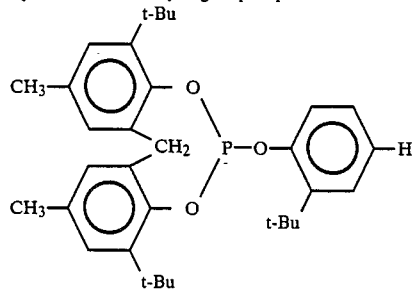

Phosphite D - A tertiary organophosphite of the formula:

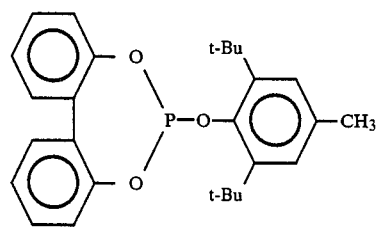

Phosphite E - A tertiary organophosphite of the formula:

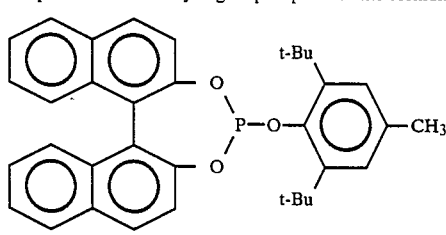

Phosphite F - A tertiary organophosphite of the formula:

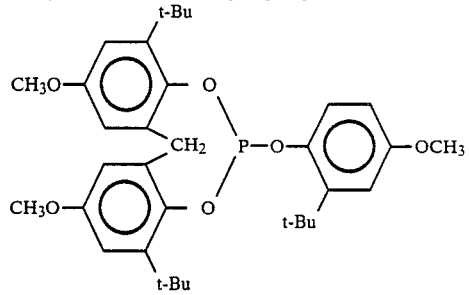

Texanol ® - 2,2,4-trimethyl-1,3-pentanediol monoisobutyrate
pka - Measure of the strength of the base as shown in "Dissociation Constants of Organic Bases in Aqueous Solution by D. D. Perrin, Butterworth, LKondon, 1965.
tBu - tertiary butyl radical In the following examples all treatments of the crude phosphite compositions, unless otherwise noted, were conducted under nitrogen in round-bottomed flasks equipped with a magnetic stirring bar, reflux condenser and gas adapter attached by a T-connection to a nitrogen source and a mineral oil bath bubbler.

The, $^{31}$Phosphorus Nuclear Magnetic Resonance ($^{31}$p NMR) analysis data in all the examples, unless otherwise indicated, were obtained by using a nitrogen-flushed 10 mm NMR tube and tetrahydrofuran as the NMR diluent. The NMR data in all the examples is expressed as percent of total peak height, which may be converted to mole percent by multiplying the peak height of the tertiary organophosphite employed divided by the peak height of its corresponding secondary organophosphite with the Response Factor of the tertiary organophosphite employed. For example $$\frac{\text{Peak height of Tertiary Phosphite}}{\text{Peak height of Secondary Phosphite}} \times R.F. = \frac{\text{Moles of Tertiary Phosphite}}{\text{Moles of Secondary Phosphite}}$$

The Response Factor of a given tertiary organophosphite is determined by obtaining a $^{31}$P NMR spectrum of a mixture of know molar composition of tertiary and secondary organophosphite i.e.

$$R.F. = \frac{\text{Moles of Tertiary Phosphite}}{\text{Moles of Secondary Phosphite}} \times \frac{\text{Peak height of Secondary Phosphite}}{\text{Peak height of Tertiary Phosphite}}$$

For instance the R.F. of Phosphite A is 1.71; the R.F. of Phosphite B is 1.18 and the R.F. of triphenylphosphite is 1.72.

TPPO, i.e., triphenylphosphine oxide used as an internal standard in same $^{31}$P NMR in some examples to keep track of the concentration of tertiary organophosphite.

EXAMPLE 1

Seven ml. of acetonitrile and 3.5 grams of crude Phosphite A, (about 7% being its corresponding secondary organophosphite) were charged to a round-bottomed flask. The flask was placed in an oil bath and in the following order, about 0.5 ml (3.6 mmol.) of triethylamine and 0.5 ml. (27.8 mmol) of water were added as the flask was warmed to reflux temperature. Upon reaching reflux, since all of the solids had not dissolved, 4 ml. of more acetonitrile were added after 5 minutes and a further 4 ml. were added after 30 minutes. After 1.25 hours the flask was removed from the oil bath. A 1 ml. sample was withdrawn from the flask and subjected to $^{31}$P NMR analysis. The NMR analysis showed that Phosphite A remained intact while the corresponding secondary organophosphite was completely converted to its corresponding primary organophosphite salt.

Moreover, white needle-like crystals precipitated out of the reaction solution in the flask upon standing at room temperature, and after about 20 hours the crystals were collected by filtration, washed with 5 ml of cold (about 0° C.) acetonitrile and dried in vacuo to afford about 2.5 grams of the white crystals which $^{31}$P NMR analysis confirmed to be purified Phosphite A, all traces of primary and secondary organophosphite having been removed by said crystallization. The results are summarized in the following table.

TABLE I

| Sample Composition | $^{31}$P NMR DATA | | |
|---|---|---|---|
|  | Percent Tertiary Phosphite | Percent Secondary Phosphite | Percent Primary Phosphite |
| Start[1] | 93 | 7 | 0 |
| Treated Solution[2] | 92 | 0 | 8 |
| Crystalline Product[3] | 100 | 0 | 0 |

[1]Crude Phosphite A Starting Composition
[2]Phosphite Solution after treatment with triethylamine and water
[3]Purified Phosphite A

EXAMPLE 2

About 1075 lbs. of crude Phosphite A (containing corresponding secondary organophosphite) was dissolved in 2345 lbs. of acetonitrile and treated with 38 lbs. of triethylamine and 100 lbs. of added water in a stirred tank reactor under nitrogen and refluxed for about 3 hours. Phosphite A was then precipitated from the reaction solution at room temperature. The precipitated product was collected by centrifugation, the cake washed with about 600 lbs. of acetonitrile and the resulting solid dried in a double cone blend drier at 50° C. under vacuum to give 1004 lbs. (about 96% yield) of desired Phosphite A product which was confirmed by $^{31}$P NMR analysis to be purified Phosphite A that was free from detectable secondary organophosphite. The results are reported in the following table

TABLE II

| Sample Composition | $^{31}$P NMR DATA | | |
|---|---|---|---|
|  | Percent Tertiary Phosphite | Percent Secondary Phosphite | Percent Primary Phosphite |
| Start[1] | 97.6 | 2.4 | 0 |
| Crystalline Product[2] | 100 | 0 | <0.1 |

[1]Crude Phosphite A Starting Composition
[2]Purified Phosphite A

EXAMPLE 3

The procedure in Example 1 was repeated using about 10 grams of crude Phosphite B, 7 ml. of acetonitrile, 0.5 ml. (3.6 mmol) of triethylamine and 0.5 ml (27.8 mmol) water. As the solution approached reflux the solids dissolved. $^{31}$P NMR analysis of the treated solution after 1.25 hours in the bath showed that Phosphite B remained intact, while the secondary organophosphite was completely converted to its corresponding primary organophosphite salt.

White needle-like crystals precipitated out of the reaction solution upon standing at room temperature and after about 20 hours, the crystals were collected by filtration, washed with 5 ml. of cold (about 0° C.) acetonitrile and dried in vacuo to afford about 7.0 grams of the white crystals which $^{31}$P NMR analysis confirmed to be purified Phosphite B, all traces of primary and secondary organophosphite having been removed by said crystallization. The results are summarized in the following table.

TABLE III

| Sample Composition | $^{31}$P NMR DATA | | |
|---|---|---|---|
|  | Percent Tertiary Phosphite | Percent Secondary Phosphite | Percent Primary Phosphite |
| Start[1] | N/A* | N/A* | N/A* |
| Treated Solution[2] | 70 | 0 | 30 |
| Crystalline Product[3] | 100 | 0 | 0 |

*Not available; No NMR of Starting Composition
[1]Crude Phosphite B Starting Composition
[2]Phosphite Solution after treatment with triethylamine and water
[3]Purified Phosphite B

EXAMPLE 4

The procedure in Example 3 was repeated using about 10 grams of crude Phosphite B, (a composite of equal weights of four contaminated samples having an average of about 6.9% corresponding secondary organophosphite as shown by $^{31}$P NMR) and 7 ml. of acetonitrile, 0.5 ml. (3.6 mmol) of triethylamine and 0.5 ml (27.8 mmol) water. As the solution approached reflux the solids dissolved. After 1.25 hours in the bath the flask was removed. White needle-like crystals precipitated out of the reaction solution upon standing at room temperature and after about 4 hours, the crystals were collected by filtration, washed with 5 ml. of cold (about 0° C.) acetonitrile and dried in vacuo to afford about 8.8 grams of the white crystals which $^{31}$P NMR analysis confirmed to be purified Phosphite B, all traces of primary and secondary organophosphite having been removed by said crystallization. The results are summarized in the following table.

TABLE IV

| Sample Composition | $^{31}$P NMR DATA | | |
|---|---|---|---|
|  | Percent Tertiary Phosphite | Percent Secondary Phosphite | Percent Primary Phosphite |
| Start[1] | 93.1 | 6.9 | 0 |
| Crystalline Product[2] | 100 | 0 | 0 |

[1]Crude Phosphite B Starting Composition (average of 4 composites).
[2]Purified Phosphite B

EXAMPLE 5

200 ml. of acetonitrile and 100 grams of crude Phosphite B, (containing corresponding secondary organophosphite) were charged to a round-bottomed flask. The flask was placed in an oil bath and in the following order, about 5 ml (68 mmol.) of triethylamine and 10 ml. (555 mmol) of water were added as the flask was warmed to reflux temperature. As the reaction solution approached reflux, the solids dissolved. After 1.25 hours in the bath the flask was removed. White needle-like crystals precipitated out of the reaction solution upon standing at room temperature and after about 20 hours the crystals were collected by filtration, washed with 500 ml of cold (about 0° C.) acetonitrile and dried in vacuo to afford about 85.35 grams of white crystals which $^{31}$P NMR analysis confirmed to be purified Phosphite B, all traces of primary and secondary organophosphite having been removed by said crystallization. The results are summarized in the following table.

TABLE V

| Sample Composition | $^{31}$P NMR DATA | | |
|---|---|---|---|
| | Percent Tertiary Phosphite | Percent Secondary Phosphite | Percent Primary Phosphite |
| Start[1] | 72 | 18 | 0 |
| Crystalline Product[2] | 100 | 0 | 0 |

[1]Crude Phosphite B Starting Composition
[2]Purified Phosphite B

EXAMPLE 6

Ten ml. of acetonitrile and a mixture of 8.0 grams of pure Phosphite A and 2 grams of corresponding secondary organophosphite, were charged to a round-bottomed flask. The flask was placed in an oil bath and in the following order, about 1.0 ml (7.2 mmol.) of triethylamine and 0.5 ml. (27.8 mmol) of water were added as the flask was warmed to reflux temperature. After 1.25 hours the flask was removed from the oil bath. White needle-like crystals precipitated out of the reaction solution upon standing at room temperature, and after about 20 hours the crystals were collected by filtration, washed with two 10 ml portions of cold (about 0° C.) acetonitrile and dried in vacuo to afford about 7.11 grams (about 89% yield) of white crystals which $^{31}$P NMR analysis confirmed to be purified Phosphite A, all traces of primary and secondary organophosphite having been removed by said crystallization. The results are summarized in the following table.

TABLE VI

| Sample Composition | $^{31}$P NMR DATA | | |
|---|---|---|---|
| | Percent Tertiary Phosphite | Percent Secondary Phosphite | Percent Primary Phosphite |
| Start[1] | 59.17 | 40.82 | 0 |
| Crystalline Product[2] | 100 | 0 | 0 |

[1]Mixture of Pure Phosphite A and Secondary Organophosphite
[2]Purified Phosphite A

EXAMPLE 7

As a comparison experiment 20 ml. of acetonitrile and a mixture of 8.0 grams of pure Phosphite A and 2 grams of corresponding secondary organophosphite, were charged to a round-bottomed flask. The flask was placed in an oil bath and heated to reflux until homogeneous. The flask was removed from the oil bath and white crystals precipitated out of the reaction solution upon standing at room temperature. When crystal formation was complete the crystals were filtered under nitrogen and washed with a few ml of cold (about 0° C.) acetonitrile and dried in vacuo to afford about 8.8 grams of recrystallized product which $^{31}$P NMR analysis showed to be Phosphite A, that was still grossly contaminated with secondary organophosphite. The results are summarized in the following table.

TABLE VII

| Sample Composition | $^{31}$P NMR DATA | | |
|---|---|---|---|
| | Percent Tertiary Phosphite | Percent Secondary Phosphite | Percent Primary Phosphite |
| Start[1] | 59.17 | 40.8 | 0 |
| Crystalline Product[2] | 62.4 | 37.5 | 0 |

[1]Mixture of Pure Phosphite A and Secondary Organophosphite Starting Composition
[2]Phosphite A Contaminated with Secondary Organophosphite

EXAMPLE 8

As a comparison experiment 20 ml. of acetonitrile and 100 grams of crude Phosphite B (containing corresponding secondary organophosphite) were charged to a round-bottomed flask. The flask was placed in an oil bath and heated to reflux until homogeneous. The flask was removed from the oil bath and white crystals precipitated out of the reaction solution upon standing at room temperature. When crystal formation was complete the crystals were filtered under nitrogen and washed with a few ml of cold (about 0° C.) acetonitrile and dried in vacuo to afford about 8.93 grams of recrystallized product which $^{31}$P NMR analysis showed to be Phosphite B, that was still grossly contaminated with secondary organophosphite. The results are summarized in the following table.

TABLE VIII

| Sample Composition | $^{31}$P NMR DATA | | |
|---|---|---|---|
| | Percent Tertiary Phosphite | Percent Secondary Phosphite | Percent Primary Phosphite |
| Start[1] | 38.27 | 61.7 | 0 |
| Crystalline Product[2] | 41.07 | 58.92 | 0 |

[1]Crude Phosphite B Starting Composition
[2]Phosphite B Contaminated with Secondary Organophosphite

EXAMPLE 9

A mixture of 10 grams of crude Phosphite B (containing corresponding secondary organophosphite) and 17 ml of acetonitrile was charged to round bottom flask followed by the addition of 3.0 ml (21.52 mmol) of triethylamine. The flask was placed in an oil bath and heated to reflux. The solution became homogeneous and 0.5 ml (27.8 mmol) of water were added. After 1.25 hours in the bath the flask was removed and the reaction solution cooled to room temperature whereupon white crystals precipitated out of the solution. When crystal formation was complete, the crystals were filtered under nitrogen and washed with three 10 ml portions of cold (about −40° C.) acetonitrile and dried in vacuo to afford about 4.36 grams of crystallized product. About a 500 mg. portion of the crystallized product was analyzed via $^{31}$P NMP and found to be purified Phosphite B that was free of secondary organophosphite, but which still contained a small amount of primary organophosphite. The remaining crystallized product (about 3.73 grams) was washed with further three 10 ml portions of cold (about 0° C.) acetonitrile and dried in vacuo to afford about 3.3 grams of crystalline product which $^{31}$P NMR analysis confirmed to be purified Phosphite B that was free of any traces of both secondary and primary organophosphite. The results are summarized in the following table.

TABLE IX

| | $^{31}$P NMR DATA | | |
|---|---|---|---|
| Sample Composition | Percent Tertiary Phosphite | Percent Secondary Phosphite | Percent Primary Phosphite |
| Start[1] | 38.29 | 61.7 | — |
| Crystalline Product I[2] | 97.8 | 0 | 2.18 |
| Crystalline Product II[3] | 100 | 0 | 0 |

[1]Crude Phosphite B Starting Composition
[2]Purified Phosphite B after washing with −40° C. acetonitrile
[3]Purified Phosphite B after further washing with 0° C. acetonitrile

EXAMPLE 10

Five ml. of acetonitrile and 0.93 grams of crude Phosphite C, (containing corresponding secondary organophosphite) were charged to a round-bottomed flask. The flask was placed in an oil bath and in the following order, about 0.5 ml (3.6 mmol.) of triethylamine and 0.2 ml. (11.11 mmol) of water were added as the flask was warmed to reflux temperature. After 1.25 hours the flask was removed from the oil bath. A 1 ml. sample was withdrawn from the flask and subjected to $^{31}$P NMR analysis. The NMR analysis indicated that most of Phosphite C had been converted to secondary phosphite. The results are summarized in the following table.

TABLE X

| | $^{31}$P NMR DATA | | |
|---|---|---|---|
| Sample Composition | Percent Tertiary Phosphite | Percent Secondary Phosphite | Percent Primary Phosphite |
| Start[1] | 42.05 | 57.9 | 0 |
| Treated Solution[2] | 15.52 | 84.47 | 0 |

[1]Crude Phosphite C Starting Composition
[2]Phosphite Solution after treatment with triethylamine and water

EXAMPLE 11

Five ml. of acetonitrile and 1.0 gram of crude Phosphite D, (containing corresponding secondary organophosphite) were charged to a round-bottomed flask. The flask was placed in an oil bath and in the following order, about 0.5 ml (3.6 mmol.) of triethylamine and 0.2 ml. (11.11 mmol) of water were added as the flask was warmed to reflux temperature. After 1.25 hours the flask was removed from the oil bath. A 1 ml. sample was withdrawn from the flask and subjected to $^{31}$P NMR analysis. The NMR analysis showed that both phosphites were converted to primary phosphite salt. The results are summarized in the following table.

TABLE XI

| | $^{31}$P NMR DATA | | |
|---|---|---|---|
| Sample Composition | Percent Tertiary Phosphite | Percent Secondary Phosphite | Percent Primary Phosphite |
| Start[1] | 55.12 | 44.8 | 0 |
| Treated Solution[2] | 0 | 0 | 100 |

[1]Crude Phosphite D Starting Composition
[2]Phosphite Solution after treatment with triethylamine and water

EXAMPLE 12

Fifteen ml. of tetrahydrofuran and 1.0 gram of crude Phosphite D, (containing corresponding secondary organophosphite) along with triphenylphosphine oxide as an internal standard were charged to a round-bottomed flask. The flask was placed in an oil bath and in the following order, about 3.0 ml (21.52 mmol.) of triethylamine and 0.2 ml. (11.11 mmol) of water were added as the flask was warmed to reflux temperature. After 1.25 hours the flask was removed from the oil bath. A 1 ml. sample was withdrawn from the flask and subjected to $^{31}$P NMR analysis. The NMR analysis showed that most of the secondary organophosphite was converted to primary organophosphite salt while nearly all of Phosphite D remained intact. The results are summarized in the following table.

TABLE XII

| | $^{31}$P NMR DATA | | | |
|---|---|---|---|---|
| Sample Composition | Percent Tertiary Phosphite | Percent Secondary Phosphite | Percent TPPO | Percent Primary Phosphite |
| Start[1] | 56.4 | 43.46 | a | 0 |
| Treated Solution[2] | 53.6 | 0 | — | 46.4 |

[1]Crude Phosphite D Starting Composition
[2]Phosphite Solution after treatment with triethylamine and water
[a]Some precipitate formed during the addition of triethylamine throwing off calibration vs. internal standard (TPPO).

EXAMPLE 13

Ten ml. of tetrahydrofuran and 1.0 gram of crude Phosphite D, (containing corresponding secondary organophosphite) along with triphenylphosphine oxide as an internal standard were charged to a round-bottomed flask. The flask was placed in an oil bath and in the following order, about 2 grams of Puramer ® S and 0.2 ml. (11.11 mmol) of water were added as the flask was warmed to reflux temperature. After 1.25 hours the flask was removed from the oil bath. A 1 ml. sample, minus the insoluble Puramer ® S and primary organophosphite salt sequestered thereon, was withdrawn from the flask and subjected to $^{31}$P NMR analysis. The NMR analysis showed that all secondary organophosphite was converted to primary organophosphite salt while all of Phosphite D remained intact. The results are summarized in the following table.

TABLE XIII

| | $^{31}$P NMR DATA | | | |
|---|---|---|---|---|
| Sample Composition | Percent Tertiary Phosphite | Percent Secondary Phosphite | Percent TPPO | Percent Primary Phosphite |
| Start[1] | 36.23 | 17.9 | 45.87 | 0 |
| Treated Solution[2] | 45.9 | 0 | 54.09 | 0[a] |

[1]Crude Phosphite D Starting Composition
[2]Phosphite Solution after treatment with Puramer ® S and water
[a]No solid primary phosphite salt in NMR sample.

EXAMPLE 14

15 ml. of tetrahydrofuran and 1.0 grams of crude Phosphite E, (containing corresponding secondary organophosphite) along with triphenylphosphine oxide as an internal standard were charged to a round-bottomed flask. The flask was placed in an oil bath and in the following order, about 2.0 grams of Puramer ® S and 0.2 ml. (11.11 mmol) of water were added as the flask was warmed to reflux temperature. After 1.25 hours the flask was removed from the oil bath. A 1 ml. sample, minus the insoluble Puramer ® S and primary organophosphite salt sequestered thereon, was withdrawn from the flask and subjected to $^{31}P$ NMR analysis. The NMR analysis showed that all secondary organophosphite was converted to primary organophosphite salt while all of Phosphite E remained intact. The results are summarized in the following table.

TABLE XIV

| Sample Composition | $^{31}P$ NMR DATA | | | |
|---|---|---|---|---|
| | Percent Tertiary Phosphite | Percent Secondary Phosphite | Percent TPPO | Percent Primary Phosphite |
| Start[1] | 72.11 | 2.45 | 25.44 | 0 |
| Treated Solution[2] | 79.72 | 0 | 20.27 | 0[a] |

[1]Crude Phosphite E Starting Composition
[2]Phosphite Solution after treatment with Puramer ® S and water
[a]No solid primary phosphite salt in NMR sample.

EXAMPLE 15

15 ml. of tetrahydrofuran and 1.0 gram of crude Phosphite F, (containing corresponding secondary organophosphite) along with triphenylphosphine oxide as an internal standard were charged to a round-bottomed flask. The flask was placed in an oil bath and in the following order, about 2.0 grams of Puramer ® S and 0.2 ml. (11.11 mmol) of water were added as the flask was warmed to reflux temperature. After 1.25 hours the flask was removed from the oil bath. A 1 ml. sample, minus the insoluble Puramer ® S and primary organophosphite salt sequestered thereon, was withdrawn from the flask and subjected to $^{31}P$ NMR analysis. The NMR analysis showed that most of the secondary organophosphite was converted to primary organo phosphite salt while most of Phosphite F remained intact. The results are summarized in the following table.

TABLE XV

| Sample Composition | $^{31}P$ NMR DATA | | | |
|---|---|---|---|---|
| | Percent Tertiary Phosphite | Percent Secondary Phosphite | Percent TPPO | Percent Primary Phosphite |
| Start[1] | 32.31 | 49.03 | 18.65 | 0 |
| Treated Solution 2 | 50.82 | 13.08 | 36.08 | 0[a] |

[1]Crude Phosphite F Starting Composition
[2]Phosphite Solution after treatment with Puramer ® S and water
[a]No solid primary phosphite salt in NMR sample.

EXAMPLE 16

Ten ml. of tetrahydrofuran and 1.0 gram of crude Phosphite F, (containing corresponding secondary organophosphite) along with triphenylphosphine oxide as an internal standard were charged to a round-bottomed flask. The flask was placed in an oil bath and in the following order, about 3.0 ml (21.52 mmol) of triethylamine and 0.2 ml. (11.11 mmol) of water were added as the flask was warmed to reflux temperature. After 1.25 hours the flask was removed from the oil bath. A 1 ml. sample was withdrawn from the flask and subjected to $^{31}P$ NMR analysis. The NMR analysis showed that all secondary organophosphite was converted to primary organo phosphite salt while all of Phosphite F remained intact. The results are summarized in the following table.

TABLE XVI

| Sample Composition | $^{31}P$ NMR DATA | | | |
|---|---|---|---|---|
| | Percent Tertiary Phosphite | Percent Secondary Phosphite | Percent TPPO | Percent Primary Phosphite |
| Start[1] | 34.15 | 41.41 | 24.43 | 0 |
| Treated Solution[2] | 31.56 | 0 | 24.37 | 44.0 |

[1]Crude Phosphite F Starting Composition
[2]Phosphite Solution after treatment with triethylamine and water

EXAMPLES 17 TO 21

A series of experiments were carried out demonstrating the selective conversion of diphenylphosphite to primary organophosphite in the presence of triphenylphosphite using a soluble amine and water. Said experiments also demonstrate that the primary phosphite salt must be separated from the tertiary triphenylphosphite if the triphenylphosphite is to be stabilized since the primary phosphite induces rapid decomposition of the triphenylphosphite even at room temperature.

The experiments were carried out by charging 0.311 grams (1.13 mmol) of diphenyl phosphite, 0.723 grams (2.26 mmol) of triphenylphosphite and 4 ml of acetonitrile to a round-bottomed flask. The flask was placed in an oil bath and triethylamine in the amounts specified in the table below and 0.1 ml (5.55 mmol) of water were added and the reaction solution stirred at the indicated temperature for the indicated time. A 1 ml sample of each experiment was withdrawn and subjected to $^{31}P$ NMR analysis. The results are summarized in the following table.

TABLE XVII

| Example No. | Triethyl Amine (M mol) | Temp. | Time | $^{31}P$ NMR DATA | | |
|---|---|---|---|---|---|---|
| | | | | Percent Tertiary Phosphite | Percent Secondary Phosphite | Percent Primary Phosphite |
| | Starting Composition | | | 50.6 | 49.4 | 0 |
| 17[b] | 1.69[c] | Reflux | 1.5 hrs. | 0 | 100 | — |
| 18[a] | 5.07[d] | Reflux | 1.5 hrs. | 18.3 | 2.4 | 79.3 |
| 19[a] | 22.6[e] | 25° C. | 6.0 hrs. | 68.6 | 0 | 31.4 |
| 20[a] | 22.6[e] | Reflux | 15 min. | 6.5 | 0 | 93.5 |
| 21[a] | 22.6[e] | Reflux | 75 min. | 2.4 | 0 | 97.6 |

[a]Reagents added in the following order: Triphenylphosphite, acetonitrile, triethylamine, diphenylphosphite, water
[b]Reagents added in the following order: Diphenylphosphite, triphenylphosphite, acetonitrile, triethylamine, water
[c]1.5 moles of triethylamine per mole of secondary diphenylphosphite
[d]4.5 moles of triethylamine per mole of secondary diphenylphosphite
[e]30 moles of triethylamine per mole of secondary diphenylphosphite.

EXAMPLES 22 to 25

A series of experiments were carried out demonstrating the selective conversion of diphenylphosphite using an insoluble amine resin in the presence of triphenylphosphite to primary phosphite.

The experiments were carried out by charging 9 ml of tetrahydrofuran, 0.723 grams (2.26 mmol) of triphenylphosphite and 0.4 grams of triphenylphosphine oxide as an internal standard to a round bottom flask. A 1 ml. sample was withdrawn and analyzed by $^{31}P$ NMR, the results being 36.1% Internal Standard (TPPO) and 63.95% Tertiary Phosphite. The flask was placed in an oil bath and one gram of Puramer ® S was added followed by 0.311 gram (1.13 mmol) of diphenylphosphite and 0.1 ml (5.55 mmol) of water, and the reaction mixture was stirred at the indicated temperature for the indicated time given in the table below. A 1 ml sample of the reaction solution of each experiment, minus the insoluble Puramer ® S and primary organophosphite salt requested thereon, was withdrawn and subjected to $^{31}P$ NMR analysis. The results are shown in the following table.

TABLE XVIII

| | | | $^{31}P$ NMR DATA | | | |
|---|---|---|---|---|---|---|
| Example No. | Temp. | Time | Percent Internal Standard (TPPO) | Percent Tertiary Phosphite | Percent Secondary Phosphite | Percent Primary Phosphite |
| Starting Composition[d] | | | — | 50.6 | 49.4 | — |
| 22 | 25° C. | 2 hrs. | 39 | 61 | 0 | 0[c] |
| 23 | 25° C. | 3 hrs. | 26.5[a] | 73.5 | 0 | 0[c] |
| 24 | 50° C. | 1.5 hrs. | 36.0[b] | 64 | 0 | 0[c] |
| 25 | 50° C. | 2.75 hrs. | 36.3[b] | 63.7 | 0 | 0[c] |

[a] Artificially low because of broadening of TPPO peak
[b] TPPO/Triphenylphosphite Peak height ratio unchanged
[c] No solid primary phosphite salt in NMR sample
[d] NMR analysis of a solution containing the same amounts of tertiary and secondary phosphites employed and in the absence of TPPO.

EXAMPLE 26

A nitrogen flushed 10 mm NMR tube was charged with 0.74 g triphenylphosphite (contaminated with corresponding secondary phosphite), 4.0 ml acetonitrile, 0.5 ml triethylamine, 0.1 ml distilled water and 0.102 gm triphenylphosphine oxide as internal standard, shaken well and allowed to stand at room temperature. A sample was analyzed by $^{31}P$ NMR after 2 hours, which showed that all of the secondary phosphite had been decomposed, as had a substantial portion of the tertiary phosphite. The results are shown in the following table.

TABLE XIX

| | $^{31}P$ NMR DATA | | | |
|---|---|---|---|---|
| Sample Composition | Percent Internal Standard (TPPO) | Percent Tertiary Phosphite | Percent Secondary Phosphite | Percent Primary Phosphite |
| Starting Composition | 16.2 | 50.2 | 33.5 | 0 |
| Treated Solution[1] | 9.2 | 17.6 | 0 | 73.2 |

[1] Phosphite solution after treatment with triethylamine and water

EXAMPLE 27

20 ml of tetrahydrofuran, 0.726 grams (2.26 mmol) of pure triphenylphosphite and 0.4 grams of triphenylphosphine oxide as an internal standard were charged to a round-bottomed flask. And the flask placed in an oil bath. A one ml sample was withdrawn and analyzed by $^{31}P$ NMR. One gram of Puramer ® S was then added to the flask followed by 0.1 ml (5.55 mmol) of water, and the mixture stirred at room temperature for 1.5 hours. A 2 ml sample of the reaction solution, minus the insoluble Puramer ® S and primary organophosphite salt sequestered thereon, was withdrawn and analyzed by $^{31}P$ NMR which did not detect any of the secondary or primary phosphite. Triethylamine and water (0.5 and 0.1 ml, respectfully) were then added to the flask and the reaction mixture stirred for an additional 4 hours at room temperature. A sample, minus the insoluble Puramer ® s and primary organophosphite salt sequestered thereon, was taken and analyzed by $^{31}P$ NMR, and again so secondary or primary phosphite was detected. The Puramer ® S was then removed from solution by filtration through a medium porosity frit and additional triethylamine and water were added (0.5 and 0.1 ml respectively). After an additional 1.5 hours at room temperature, a sample was taken and analyzed by $^{31}P$ NMR and still no secondary or primary phosphite was detected. After an additional 15 hours at room temperature another sample was taken and $^{31}P$ NMR indicated a small amount of decomposition of the triphenylphosphite. The results are given in the following table.

TABLE XX

| | $^{31}P$ NMR DATA | | | |
|---|---|---|---|---|
| Sample Composition | Percent Internal Standard (TPPO) | Percent Tertiary Phosphite | Percent Secondary Phosphite | Percent Primary Phosphite |
| Start[1] | 36.7 | 63.3 | 0 | 0 |
| First Sample[2] | 38.7 | 61.3 | 0 | 0 |
| Second Sample[3] | 39.2[a] | 60.8 | 0 | 0 |
| Third Sample[4] | 37.8 | 62.2 | 0 | 0 |
| Fourth Sample[5] | 38 | 51.31 | 0 | 10.7 |

[1] Starting Composition
[2] After 1.5 hours at 25° C.
[3] After 5.5 hours at 25° C.
[4] After 7.5 hours at 25° C.
[5] After 22 hours at 25° C.

EXAMPLE 28

As a comparative experiment 2.0 grams of crude Phosphite B (containing corresponding secondary organophosphite), and 4 ml. of acetonitrile were charged to a round-bottomed flask. The flask was placed in an oil bath and 0.157 grams (1.55 mmol) of triethylamine was added as the flask was warmed to reflux temperature. After 0.5 hours in the bath the flask was removed and a 1 ml. sample of the reaction solution withdrawn and analyzed by $^{31}P$ NMR which showed that little, if any, of the secondary organophosphite had been converted to primary organo phosphite. The results are given in the following table.

TABLE XXI

| | $^{31}P$ NMR DATA | | |
|---|---|---|---|
| Sample Composition | Percent Tertiary Phosphite | Percent Secondary Phosphite | Percent Primary Phosphite |
| Start[1] | 62.22 | 37.7 | 0 |
| Treated[2] Solution | 54.4 | 45.6 | 0 |

[1] Crude Phosphite B Starting Composition
[2] Reaction Solution after treatment with only triethylamine and no added water

EXAMPLE 29

As a comparative experiment 2.0 grams of crude Phosphite B (containing corresponding secondary organophosphite), and 4 ml. of acetonitrile were charged to a round-bottomed flask. The flask was placed in an oil bath and 0.1 ml (5.55 mmol) of water was added as the flask was warmed to reflux temperature. After 0.5 hours in the bath the flask was removed and a 1 ml. sample of the reaction solution withdrawn and analyzed by $^{31}$P NMR which showed that little, if any, of the secondary organophosphite had been converted to primary organo phosphite while all of the tertiary phosphite had decomposed. The results are given in the following table.

TABLE XXII

| | $^{31}$P NMR DATA | | |
|---|---|---|---|
| Sample Composition | Percent Tertiary Phosphite | Percent Secondary Phosphite | Percent Primary Phosphite |
| Start[1] | 62.22 | 37.7 | 0 |
| Treated[2] Solution | 0 | 97.84 | 2.15 |

[1]Crude Phosphite B Starting Composition
[2]Reaction Solution after treatment with only water and no added amine

EXAMPLES 30–33

A series of experiments were carried out varying the amount of triethylamine employed.

2.0 grams of crude Phosphite B (contaminated with about 1.13 mmol of the corresponding secondary phosphite) and 4 ml. of acetonitrile were charged to a round-bottomed flask. The flask was placed on an oil bath. The indicated amount of triethylamine showed in the table below, and 0.1 ml (5.55 mmol) of water were added as the flask was warmed to reflux temperature. After 1.5 hours in the bath the flask was removed and a 1 ml sample was withdrawn in each experiment. Each sample was then analyzed by $^{31}$P NMR and the results are given in the following table.

TABLE XXIII

| | | $^{31}$P NMR DATA | | |
|---|---|---|---|---|
| Example No. | Triethyl-amine (mmol) | Mole Ratio Amine/Secondary Phosphite | Percent Tertiary Phosphite | Percent Secondary Phosphite | Percent Primary Phosphite |
| Starting Composition | | | 63 | 37 | 0 |
| 30 | 2.26 | 2.0 | 64.9 | 0 | 35.1 |
| 31 | 1.13 | 1.0 | 56.88 | 0 | 43.1 |
| 32 | 0.565 | 0.5 | 16.38 | 66.6 | 17 |
| 33 | 0.113 | 0.1 | 0.38 | 99.62 | 0 |

EXAMPLES 34–39

A series of experiments were carried out varying the amounts of both the triethylamine and water added.

2.0 grams of crude Phosphite B (contaminated with about 1.13 mmol of the corresponding secondary phosphite) and 4 ml. of acetonitrile were charged to a round-bottomed flask. The flask was placed on an oil bath. The amounts of triethylamine and water were added as the flask was warmed to reflux temperature. After 1.5 hours in the bath the flask was removed and a 1 ml sample was withdrawn in each experiment. Each sample was then analyzed by $^{31}$P NMR and the results are given in the following table.

TABLE XXIV

| | | | | $^{31}$P NMR DATA | | |
|---|---|---|---|---|---|---|
| Example No. | Triethyl-Amine (mmol) | Water (mmol) | Mole Ratio Amine/Secondary Phosphite | Mole Ratio Water/Secondary Phosphite | Percent Tertiary Phosphite | Percent Secondary Phosphite | Percent Primary Phosphite |
| Starting Composition | | | | | 62.98 | 37 | 0 |
| 34 | 1.13 | 5.55 | 1.0 | 4.9 | 64.34 | 0 | 35.6 |
| 35 | 1.13 | 2.77 | 1.0 | 2.45 | 65.4 | 0 | 34.5 |
| 36 | 0.565 | 5.55 | 0.5 | 4.9 | 0 | 85.23 | 14.76 |
| 37 | 0.565 | 2.77 | 0.5 | 2.45 | 0 | 70.82 | 29.2 |
| 38 | 1.695 | 1.13 | 1.5 | 1.0 | 45.17 | 40.92 | 13.9 |
| 39 | 0.565 | 1.13 | 0.5 | 1.0 | 57.1 | 0.91 | 41.97 |

EXAMPLE 40

Various 2.0 gram batches of crude Phosphite B (as reported in the following table), and 4 ml. of acetonitrile (unless otherwise noted) were charged to a round-bottomed flask. The flask was placed in an oil bath. The indicated amounts of the various bases shown in the table below and the indicated amount of water were added as the flask was warmed to reflux temperature. After 1.25 hours in the bath the flask was removed and 1 ml. samples of each experiment withdrawn and analyzed by $^{31}$P NMR. The results are shown in the following table.

TABLE XXV

| | | $^{31}$P NMR DATA | | | | |
|---|---|---|---|---|---|---|
| Run No. | Base (mmol) | pKa | Water (mmol) | Percent Tertiary Phosphite | Percent Secondary Phosphite | Percent Primary Phosphite |
| | Starting Composition | | | 62.98 | 37 | 0 |
| 1 | Tributylamine (1.7) | 11.04 | 5.55 | 61.34 | 0 | 38.65 |
| 2 | Pyridine (1.7) | 5.25 | 5.55 | 0.98 | 99 | broad peak |
| 3 | Imidazole (1.7) | 7.0 | 5.55 | 68 | 0 | 32 |
| 4 | Triphenylamine (1.7) | −5.0 | 5.55 | 0 | 95.76 | 4.23 |
| 5 | 8-Hydroxyquinoline (1.7) | 5.0 | 5.55 | 0 | 100 | broad peak |
| 6 | 2-Hydroxypyridine (1.7) | 0.75 | 5.55 | 0 | 93.25 | 6.74 |
| | Starting Composition | | | 62.11 | 37.88 | 0 |
| 7 | Triethanolamine (1.63) | 7.5 | 11.11 | 59.75 | 2.93 | 37.28 |

TABLE XXV-continued

$^{31}$P NMR DATA

| Run No. | Base (mmol) | pKa | Water (mmol) | Percent Tertiary Phosphite | Percent Secondary Phosphite | Percent Primary Phosphite |
|---|---|---|---|---|---|---|
| 8 | Na$_2$CO$_3$ (1.5) | 10.25 | 11.11 | 57.33 | 12.85 | 29.81 |
| 9 | NaHCO$_3$ (1.5) | 6.37 | 11.11 | 45.71 | 33.82 | 20.46 |
| 10 | Dibutylamine (1.44) | 11.3 | 11.11 | 63.29 | 0 | 36.71 |
| 11 | Tetraethylammonium benzoate (2.44) | 4.2 | 11.11 | 68.49 | 0 | 31.51 |
| 12 | Tetraethylphosphonium acetate (2.6) | 4.7 | 11.11 | 67.49 | 0 | 32.5 |
| 13 | Tetraethylammonium p-toluene sulfonate (2.57) | <4 | 11.11 | 0 | 57.14 | 42.8 |
| 14 | Tetropropylammonium hydroxide (3.08) | 14.0 | 11.11 | 30.2 | 16.61 | 53.14 |
| 15 | Tetrabutylammonium tetrafluoroborate (2.66) | — | 11.11 | 0 | 100 | 0 |
| 16 | Tetrabutylammonium tetrabutylborate (2.59) | — | 11.11 | 44.4 | 11.1 | 44.4 |
| 17 | Tetramethylammonium iodide (2.58) | <4 | 11.11 | 0 | 69.25 | 30.74 |
| 18 | Ammonium tetrafluoro borate (2.67) | <4 | 11.11 | 0 | 100 | 0 |
|  | Starting Composition |  |  | 49.5 | 50.5 | 0 |
| 19 | NaOH (1.95) | 14.0 | 16.66 | 45.94 | 0 | 54 |
| 20 | NaOH (1.95)* | 14.0 | 16.66 | 46.5 | 0 | 53.4 |
| 21 | 2,6-di-t-pyridine (1.7) | 5.6 | 5.55 | 0 | 100 | 0 |
|  | Starting Composition |  |  | 63.29 | 36.7 | 0 |
| 24 | Amberlyst ® A-21 (1.5 gr) | — | 5.55 | 99.37 | 0.62 | 0$^a$ |
| 25 | Puramer ® S (1.5 gr) | — | 5.55 | 97.2 | 0 | 2.8$^b$ |

*Tetrahydrofuran solvent
$^a$No insoluble solid resin or solid primary phosphite salt in NMR sample.
$^b$Small amount of primary phosphite salt in NMR sample, most of primary phosphite salt was absorbed on the insoluble solid resin which was not present in the NMR sample.

EXAMPLES 41–46

A series of experiments were carried out varying the reaction temperature employed.

2.0 grams of crude Phosphite B (contaminated with corresponding secondary organophosphite) and 4 ml. of actonitrile were charged to a round-bottomed flask. The flask was placed on an oil bath and 1.5 grams of Puramer ® S and 0.1 ml. (5.55 mmol) of water were added to the flask. The flask was placed on an oil bath and maintained at the indicated reaction temperature for the indicated time given in the following table, after which a sample of the reaction solution, minus the insoluble Puramer ® s and primary organophosphite salt sequestered thereon, was withdrawn and analyzed by $^{31}$P NMR. Example 45 employed 2 grams of Puramer ® S instead of 1.5 grams. Examples 45 and 46 employed 4 ml of tetrahydrofuran as the solvent instead of acetonitrile, while Example 46 employed 1.5 mmoles of triethylamine instead of Puramer ® S and also Osed 11.11 mmols of water. The results are given in the following table.

TABLE XXVI

$^{31}$P NMR

| Example No. | Reaction Temp. | Time | Percent Tertiary Phosphite | Percent Secondary Phosphite | Percent Primary Phosphite |
|---|---|---|---|---|---|
| Starting Composition |  |  | 55.86 | 44 |  |
| 41 | 25° C.* | 1.25 hr. | 43 | 52.21 | 4.5$^a$ |
| 42 | 50° C. | 1.25 hr. | 91.31 | 0 | 8.68$^a$ |
| 43 | 70° C. | 1.25 hr. | 94.35 | — | 5.65$^a$ |
| 44 | 120° C. | 1.25 hr. | 96.87 | — | 3.1$^a$ |
| 45 | 25° C. | 7. hr.** | 97.84 | — | 2.16$^a$ |
| 46 | 25° C. | 1.5 hr. | 59.54 | — | 40.4 |

*No reaction. Reactants not soluble.
**Longer time relative to Ex. 46 does not indicate a slower reaction rate, but merely reflects time that the NMR was taken.
$^a$Small amount of primary organophosphite salt in the NMR sample.

EXAMPLE 47

A mixture of 3.87 mmol of Phosphite B and 1 mmol of corresponding secondary phosphite was placed in a round-bottomed flask under nitrogen with 50 ml. of anhydrous ethanol. One to two drops of 0.1% phenolphthalein in ethanol were added and about 10 ml. of 0.1 N sodium hydroxide was added at room temperature until a pink color persisted. 20 additional ml of 0.1 N sodium hydroxide were added and the reaction solution maintained at room temperature. Samples of the reaction solution were analyzed by $^{31}$P NMR at various time intervals and the results are shown in the following table.

TABLE XXVII

$^{31}$P NMR DATA

| Sample Composition | Time of Analysis | Percent Tertiary Phosphite | Percent Secondary Phosphite | Percent Primary Phosphite |
|---|---|---|---|---|
| Starting Composition |  | 62.27 | 37.7 | 0 |
| (a) | 70 min. | 30.95* | 0 | 59.52 |

TABLE XXVII-continued

| | | 31P NMR DATA | | |
|---|---|---|---|---|
| Sample Composition | Time of Analysis | Percent Tertiary Phosphite | Percent Secondary Phosphite | Percent Primary Phosphite |
| (b) | 100 min. | 10.31 | 0 | 66.52 |

*Transesterification of Phosphite B was readily apparent from the formation of an additional 9.52% of other phosphorus compounds (new peak 134.13).
**In addition to most of Phosphite B being decomposed, transesterification was readily apparent from an additional 7.58% of other phosphorus compounds (new Peak 134.13).

A similar experiment was carried out using 3.86 mmoles of Phosphite A and 0.98 mmols of corresponding secondary organophosphite. $^{31}$p NMR analysis after the solution had been maintained at room temperature for 300 minutes showed 18.03% Tertiary Phosphite, 0% Secondary Phosphite and 83.32% Primary Phosphite indicating that nearly all of Phosphite A had decomposed.

The above data represents a comparative experiment employing the addition of only sodium hydroxide as reported in *Analytical Chemistry* Vol. 28, page 1765 (1956).

EXAMPLE 48

This experiment demonstrates that the reaction product of the base-water treatment of this invention is the amine salt of the primary phosphite and not a salt of the secondary phosphite.

20 ml. of acetonitrile and 2.0 grams of the secondary organophosphite of Phosphite B were charged to a round-bottomed flask. The flask was placed in an oil bath and 1.03 ml of triethylamine and 0.4 ml (2.22 mmol) of water were added as the flask was warmed to reflux temperature. After 25 minutes in the bath the flask was removed and the reaction solution stripped to dryness on a rotary evaporator. The dried recrystallized residue was dissolved in 5 ml of tetrahydrofuran and analyzed by both $^{13}$C and $^1$H NMR.

The Proton $^1$H NMR analysis showed that the plane of symmetry in the secondary phosphite was gone in the recrystallized product and integration showed the presence of one triethylammonium ion per diol unit. The most reasonable structure consistent with the analysis is the primary organophosphite shown in the equation below. The Carbon $^{13}$C NMR analysis also supported this structure.

The following proposed equation illustrates the formation of the primary phosphite from the secondary phosphite.

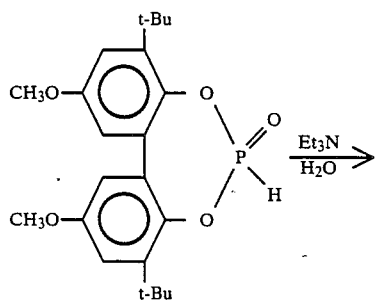

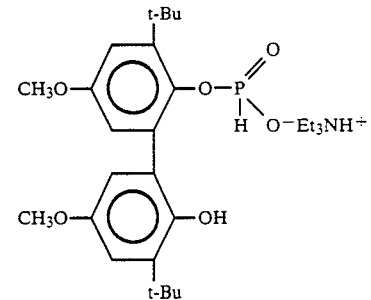

EXAMPLE 49

This experiment demonstrates that the aldehyde adducts of secondary phosphites can also be removed under conditions where the phosphites are inert.

A 250 ml flask equipped with a magnetic stirring bar and a serum stopper was charged under nitrogen flow with 12 grams of the secondary organophosphite of Phosphite B and 80 ml of mixed valeraldehyde. The flask was evacuated and heated at 120° C. for three hours, whereupon it was vented to nitrogen. Analysis of this solution by $^{31}$P NMR showed that most of the secondary phosphite had been converted to its aldehyde adduct.

2.0 ml of the above prepared aldehyde adduct solution and 4.8 grams of Texanol: were charged to a round-bottomed flask. The flask was placed on an oil bath and 0.2 ml of triethylamine and 0.1 ml (5.55 mmol) of water were added as the flask was warmed to reflux temperature. After one hour in the bath the flask was removed and a 1 ml sample withdrawn. $^{31}$P NMR analysis of the sample showed that more than 90% of the valeraldehyde adduct of the secondary phosphite had been converted to primary phosphite salt. This procedure was repeated using acetonitrile as the solvent in place of the Texanol:. $^{31}$P NMR analysis of the treated solution sample showed that more than 95% of the valeraldehyde adduct of the secondary phosphite had been converted to primary phosphite salt. The results are reported in the following table.

TABLE XXVIII

| | 31P NMR DATA | | |
|---|---|---|---|
| Sample | Percent Aldehyde Adduct | Percent Secondary Phosphite | Percent Primary Phosphite |
| Start[1] | 55.12[a] | 9.37 | 0 |
| (a)* | 4.61 | 0[b] | 90.29 |
| (b)** | 2.59 | 0[c] | 90.28 |

[1]Starting Valeraldehyde Adduct Composition.
*Treated Solution Sample wherein solvent was Texanol:.
**Treated Solution Sample wherein solvent was acetonitrile.
[a]17.24% other at new peak 29.17
14.4% other at new peak 28.83
1.78% other at new peak 27.75
2.00% other at new peak 27.58
[b]5.09% other at new peak 19.01
[c]3.95% other at new peak 18.83
2.62% other at new peak 18.55

EXAMPLE 50

A series of experiments were carried out varying the solvent employed.

2.0 grams of crude Phosphite B (containing corresponding secondary phosphite) and 4 ml. of a solvent (as reported in the following table) were charged to a round-bottomed flask. The flask was placed on an oil bath and 0.24 ml (1.69 mmol) of triethylamine and 0.1 ml (5.55 mmol) of water were added as the flask was warmed to reflux temperature. After 1.5 hours in the bath the flask was removed and a 1 ml sample was withdrawn in each experiment. Each sample was then analyzed by $^{31}P$ NMR and the results are given in the following table.

TABLE XXIX

| | | $^{31}P$ NMR DATA | | |
|---|---|---|---|---|
| Run No. | Solvent | Percent Aldehyde Adduct | Percent Secondary Phosphite | Percent Primary Phosphite |
| | Start[1] | 55.85 | 44.13 | 0 |
| 1 | Tetrahydrofuran | 56.0 | 0 | 43.99 |
| 2 | Toluene | 76.62 | 0 | 27.37 |
| 3 | Ethanol[2,3] | 57.42 | 0[a] | 30.06 |
| 4 | Methanol[2,3] | 65.52[b] | 12.41[c] | 3.03 |
| 5 | Anhydrous[2,3] Methanol | 71.4[d] | 19.66 | 2.37 |
| 6 | Anhydrous[2,3] Ethanol | 73.12 | 0[e] | 3.47 |
| 7 | Valeraldehyde[2] | 72.69 | 0[f] | 12.49 |

[a]9.99% other at new peak 7.27
2.51% other at new peak 2.4
[b]1.95% other at new peak 140.14
[c]16.26% other at new peak 4.92
[d]1.27% other at new peak 140.2
[e]23.4% other at new peak 7.38
[f]1.62% other at new peak 28.98
6.01% other at new peak 19.24
7.17% other at new peak 17.99
[1]Crude Phosphite B Starting Composition
[2]Complex product slate
[3]Foul-smelling by-products Various modifications and variations of this invention will be obvious to a worker skilled in the art and it is to be understood that such modifications and variations are to be included within the purview of this application and the spirit and scope of the appended claims.

We claim:

1. A process for separating secondary organophosphite from tertiary organophosphite which comprises (1) treating a composition consisting essentially of tertiary and secondary organophosphites dissolved in an organic solvent, with added water and a Lewis base to selectively convert the secondary organophosphite to a primary organophosphite salt and (2) separating and recovering the tertiary organophosphite from said salt.

2. A process as defined in claim 1, wherein the amount of Lewis base employed is at least 0.5 moles per mole of secondary organphosphite present in the composition to be treated and wherein the amount of added water employed is at least 0.5 moles per mole of secondary organophosphite present in the composition to be treated, with the proviso that when less than a 1:1 mole ratio of Lewis Base to secondary organophosphite is employed the mole ratio of added water to Lewis base employed is less or equal to 1:1.

3. A process as defined in claim 1 wherein the amount of Lewis base employed is at least 1 mole per mole of secondary organophosphite present in the composition to be treated and wherein the amount of added water employed is at least 1 mole per mole of secondary organophosphite present in the composition to be treated.

4. A process as defined in claim 3 wherein the mole ratio of Lewis base to secondary organophosphite employed is at least about 1.5:1, and wherein the amount of water employed is greater than the amount of Lewis base employed.

5. A process as defined in claim 4, wherein the tertiary organophosphite is selected from the group consisting of triphenylphosphite, diorganophosphites, organopolyphosphites and monoorganophosphites.

6. A process as defined in claim 4, wherein the Lewis base is an anionic base having a pKa value of at least about 4.

7. A process as defined in claim 5, wherein the Lewis base is a neutral base having a pKa value of at least about 6.

8. A process as defined in claim 5, wherein the tertiary organophosphite is selected from the group consisting of diorganophosphites and bisorganophosphites.

9. A process as defined in claim 8, wherein the Lewis base is soluble in the organic solvent.

10. A process as defined in claim 8, wherein the Lewis base is insoluble in the organic solvent.

11. A process as defined in claim 9, wherein the Lewis base is sodium hydroxide.

12. A process as defined in claim 9, wherein the Lewis base is a tertiary amine that is soluble in the organic solvent.

13. A process as defined in claim 12, wherein the Lewis base is triethylamine.

14. A process as defined in claim 10, wherein the Lewis base is a solid amine-resin that is insoluble in the organic solvent.

15. A process as defined in claim 8, wherein the purified tertiary organophosphite is separated and recovered by recrystallization of the tertiary organophosphite.

16. A process as defined in claim 9, wherein the purified tertiary organophosphite is separated and recovered by recrystallization of the tertiary organophosphite.

17. A process as defined in claim 10 wherein the purified tertiary organophosphite is separated and recovered by filtration.

18. A process as defined in claim 8, wherein the solvent is selected from the group consisting of acetonitrile and tetrahydrofuran.

19. A process as defined in claim 8, wherein a rhodium-free composition is treated with the Lewis base and added water.

20. A process as defined in claim 8, wherein the composition to be treated is a liquid composition derived from a rhodium complex catalyzed hydroformylation process, said composition consisting essentially of rhodium, tertiary organophosphite, secondary organophosphite, aldehyde, and higher boiling aldehyde condensation by-products as the solvent, and wherein the Lewis base employed is an insoluble solid amine-resin.

21. A process as defined in claim 8, wherein the process treatment is carried out at a reaction temperature in the range of from about room temperature to reflux temperature.

22. A process as defined in claim 10, wherein the Lewis base is barium carbonate.

* * * * *